(12) United States Patent
Hsiao et al.

(10) Patent No.: US 12,139,465 B2
(45) Date of Patent: Nov. 12, 2024

(54) NON-FULLERENE ACCEPTOR COMPOUND CONTAINING BENZOSELENADIAZOLE AND ORGANIC OPTOELECTRONIC DEVICE INCLUDING THE SAME

(71) Applicant: RAYNERGY TEK INCORPORATION, Hsinchu (TW)

(72) Inventors: Yu-Tang Hsiao, Hsinchu (TW);
Chia-Hao Lee, Hsinchu (TW);
Chuang-Yi Liao, Hsinchu (TW);
Chun-Chieh Lee, Hsinchu (TW);
Chia-Hua Li, Hsinchu (TW);
Hsiuan-Ling Ho, Hsinchu (TW);
Yi-Ming Chang, Hsinchu (TW)

(73) Assignee: RAYNERGY TEK INCORPORATION, Hsinchu (TW)

( * ) Notice: Subject to any disclaimer, the term of this patent is extended or adjusted under 35 U.S.C. 154(b) by 209 days.

(21) Appl. No.: 17/105,673

(22) Filed: Nov. 27, 2020

(65) Prior Publication Data

US 2021/0230130 A1    Jul. 29, 2021

Related U.S. Application Data

(60) Provisional application No. 62/962,428, filed on Jan. 17, 2020.

(51) Int. Cl.
| | | |
|---|---|---|
| C07D 293/12 | (2006.01) | |
| C07D 517/22 | (2006.01) | |
| H10K 85/10 | (2023.01) | |
| H10K 50/16 | (2023.01) | |

(52) U.S. Cl.
CPC ....... *C07D 293/12* (2013.01); *H10K 85/1135* (2023.02); *H10K 50/166* (2023.02)

(58) Field of Classification Search
CPC ............................ C07D 293/12; C07D 517/22
See application file for complete search history.

(56) References Cited

FOREIGN PATENT DOCUMENTS

| CN | 103732721 A | 4/2014 | |
|---|---|---|---|
| CN | 108948042 A | 12/2018 | |
| CN | 109134513 A | 1/2019 | |
| CN | 110408010 A | 11/2019 | |
| CN | 110964040 A | 4/2020 | |
| CN | 111285885 A * | 6/2020 | ........... C07D 517/22 |
| CN | 112979682 A | 6/2021 | |
| TW | 202124394 A | 7/2021 | |

OTHER PUBLICATIONS

Zhang et al. Energy Environ. Sci. 2014, 7, 1966-1973 (Year: 2014).*
Yang et al. Energy Environ. Sci., 2012, 5, 8208-8214 (Year: 2012).*
Meriam-Webster definition of "ketone," obtained from https://www.merriam-webster.com/dictionary/ketone on Oct. 21, 2023 (Year: 2023).*
Official Action Issued By Foreign Patent Office in Application No. 11021206540/109142129.
International Search Report Issued By Foreign Patent Office in Application No. 2020198742-/874654.
"Effect of Chalcogen Atom Variation in Chalcogenadiazole Fused Indolo [2, 3-a] Carbazoles," Sirina Ghosh, et al., New J. Chem., DOI: 10.1039/C7NJ04661H. 2018.
"Synthesis of Alternating Donor-Accepted Ladder Type Molecules and Investigating Their Multiple Charge Transfer Pathways Modulated by Bandgap With Stm-Break Function," Zhengxu Cai, et al., Angew. Chem. Int. Ed., 10.1002/anie.201713323. 2018.
China National Intellectual Property Administration, First official action on Apr. 4, 2023.
Audrey Eshun et al., "Investigations of Thienoacene Molecules for Classical and Entangled Two-Photon Absorption", Sep. 25, 2018, Published by American Chemical Society.

* cited by examiner

*Primary Examiner* — Matthew P Coughlin
(74) *Attorney, Agent, or Firm* — WPAT, P.C

(57) ABSTRACT

The present invention relates to a non-fullerene acceptor compound containing benzoselenadiazole, and organic optoelectronic devices comprising the same.

12 Claims, 11 Drawing Sheets

NON-FULLERENE ACCEPTOR COMPOUND CONTAINING BENZOSELENADIAZOLE AND ORGANIC OPTOELECTRONIC DEVICE INCLUDING THE SAME

BACKGROUND OF THE INVENTION

Field of the Invention

The present invention relates to a compound, especially to a non-fullerene acceptor compound containing benzoselenadiazole and organic optoelectronic devices including the same.

Description of Related Art

In order to produce more general-purpose electronics with lower cost, there is an ever-increasing demand for organic semiconducting compounds (OSCs). Compared with conventional semiconducting materials, OSCs have features of a wide range of light absorption, high optical absorption coefficient, and adjustable structure in which a range of light absorption, energy level, and solubility are all able to be modified according to target needs. Moreover, organic materials used for manufacturing components have advantages of low cost, flexibility, lower toxicity, and large-scale production so that they have competitive advantages in respective fields. Therefore OSCs have a wide range of applications including organic field-effect transistor (OFET), Organic light-emitting diode (OLED), Organic photodetector (OPD), Organic photovoltaic (OPV) cells/batteries, sensors, storage elements, and various components or assemblies of the logic circuit. While being applied to the above-mentioned components or assemblies, organic semiconducting compounds are usually in the form of a thin film with a thickness of 50 nm to 1 Um.

An organic photodetector (OPD) is a new field of organic optoelectronics in recent years. The OPDs are made from different materials for various applications. Owing to the development of material science, OPDs not only can be produced in the form of thin films and their absorption spectrum also covers from the ultraviolet to the near-infrared (NIR) regions. Or only specific wavelengths of energy have been absorbed. For example, materials that absorb infrared light are required to circumvent interference from visible light during biometrics. Depending on the light sources of OPD products available on the market now, the light wavelength needs to be absorbed is 850 nm or 940 nm.

Since the materials for the active layer of the OPD have direct effects on the performance of the device, they play key roles in determining the device performance. The materials include donor materials and acceptor materials. The common donor materials consist of organic polymers, oligomers, or specific molecular units. Now the development of donor-acceptor (D-A) conjugated polymers is the mainstream of developing donor materials. The energy levels and band gaps of the polymer can be modulated by push-pull electronic effects resulted from the interaction between electron-rich units and electron-deficient units in the polymer. The acceptor material used in combination with the donor material usually includes fullerene derivatives with high electrical conductivity and absorption band in the 400-600 nm, graphene, metal oxides, quantum dots, etc. However, the structure of fullerene derivatives is not easy to adjust and its absorption band as well as energy level range has limitations so that the combinations of the fullerene derivatives with the donor materials are limited. Along with the development of the market, the demand for near-infrared materials is increased. Even the absorption band of the donor conjugated polymers has been shifted to the near-infrared region, the conjugated polymers are unable to have a good match due to the limitations of the fullerene acceptors. Thus, non-fullerene acceptor compounds have been developed to replace conventional fullerene acceptors used in the active layer. Thereby the development of non-fullerene acceptor compounds is an important breakthrough.

Nonetheless, it's difficult to develop non-fullerene acceptor compounds at the early stage. The compound morphology is difficult to control so that its power conversion efficiency (PCE) is on the low side. Owing to a large amount of related research after 2015, the PCE of non-fullerene acceptor compounds has been significantly improved and non-fullerene acceptor compounds have become a competitive option. The change of the PCE is due to the progress in synthesis and improvement in material design. A plurality of donor materials previously developed for fullerene acceptors is also helpful for the research and development of non-fullerene acceptor compounds.

The non-fullerene acceptor compounds are mainly designed in A-D-A (acceptor-donor-acceptor) type molecules, in which an electron-rich core unit (D) is flanked by two electron-deficient units (A). The donor (D) generally are molecules composed of benzene and thiophene while the most common acceptor (A) are cyano-indanone (IC) derivatives. In another A'-D-A-D-A' type molecules, the electron-deficient unit used as the core usually includes molecules with sulfur atoms for improving the performance.

After eliminating bottlenecks at an early stage in the field of non-fullerene acceptor compounds, non-fullerene acceptor compounds still need further development. Thus, there is room for improvement in material selection or performance and there is a need to provide novel non-fullerene acceptor compounds with smaller energy gap, better electrical properties, and higher power conversion efficiency to solve problems in the field.

SUMMARY OF THE INVENTION

Therefore it is a primary object of the present invention to provide a non-fullerene acceptor compound with a smaller gap and able to reduce leakage current and improve power conversion efficiency while being applied to organic optoelectronic devices such as organic photodetectors (OPD) and organic photovoltaic (OPV) devices.

To achieve the above object, a non-fullerene acceptor compound containing benzoselenadiazole according to the present invention is provided and has the following structural formula:

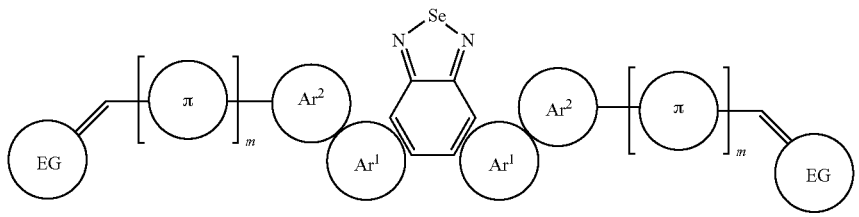

wherein Ar¹ is a five-membered heterocyclic ring; Ar² is a monocyclic or polycyclic C5-C20 heteroaromatic derivative; π is a monocyclic or polycyclic C5-C20 heteroaromatic derivative, wherein m=0-5; and EG is a monocyclic or polycyclic derivative containing ketone group and electron-withdrawing group.

Preferably, the Ar¹ is selected from the group consisting of

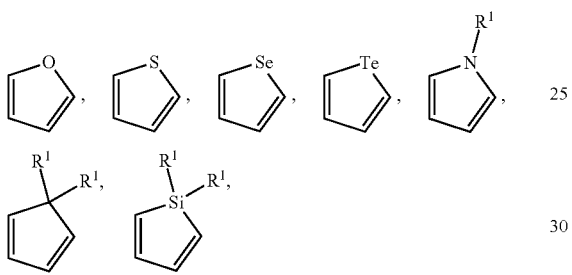

and a combination thereof. The substituent R¹ is selected from the group consisting of C1-C30 linear alkyl, C1-C30 branched alkyl, C1-C30 silyl, C1-C30 ester, C1-C30 alkoxy, C1-C30 alkylthio, C1-C30 haloalkyl, C1-C30 alkyl substituted with alkene groups or alkyne groups, C1-C30 cyanoalkyl, C1-C30 nitroalkyl C1-C30 hydroxyalkyl C1-C30 keto-alkyl, halogen, and a combination thereof.

Preferably, the Ar² is selected from the group consisting of:

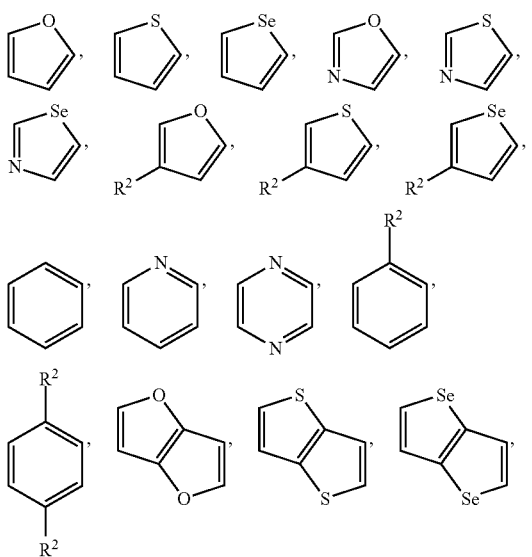

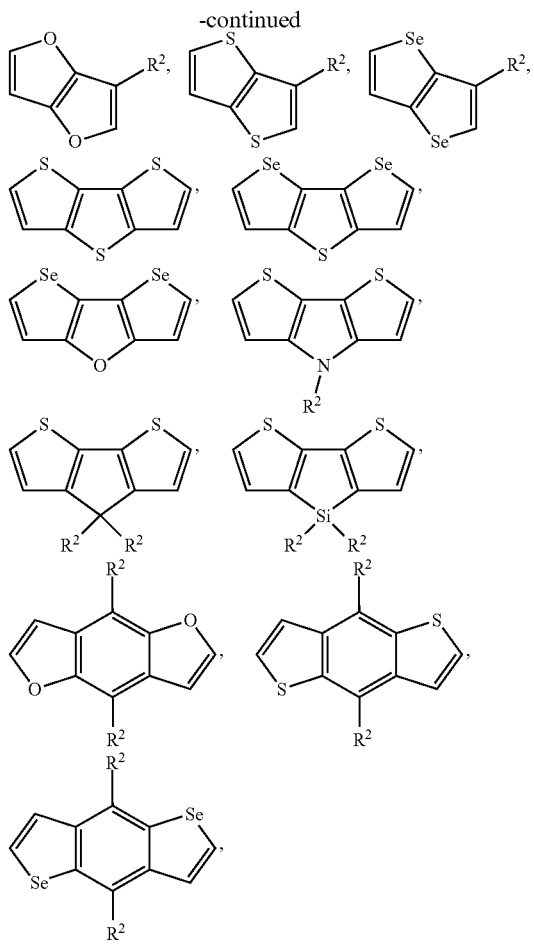

and a combination thereof, which the substituent R² of Ar² is selected from the group consisting of C1-C30 linear alkyl, C1-C30 branched alkyl, C1-C30 silyl, C1-C30 ester, C1-C30 alkoxy, C7-C30 alkylthio, C7-C30 haloalkyl, C1-C730 alkyl substituted with alkene groups or alkyne groups, C1-30 cyanoalkyl C1-C30 nitroalkyl, C1-C30 hydroxyalkyl, C1-C30 keto-alkyl, halogen, benzene ring containing R¹, five-membered heterocycle containing R¹, six-membered heterocycle containing R¹, and a combination thereof.

Preferably, the π is selected from the group consisting of

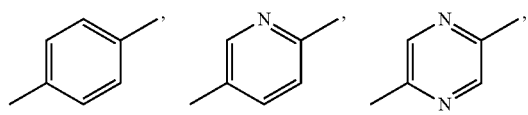

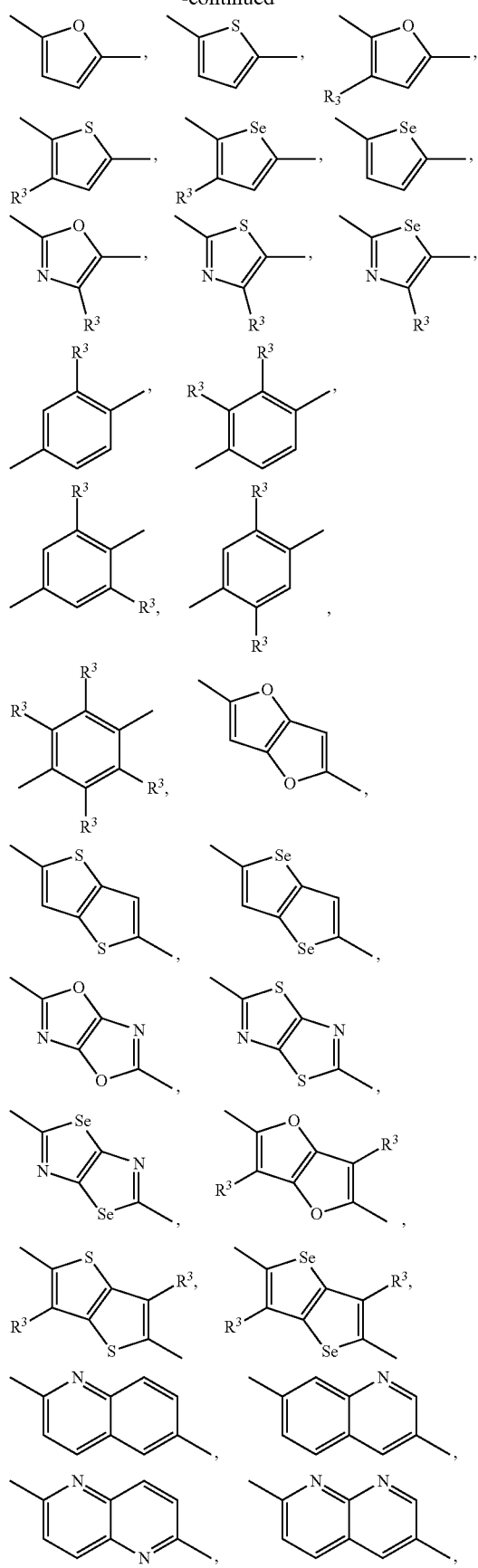
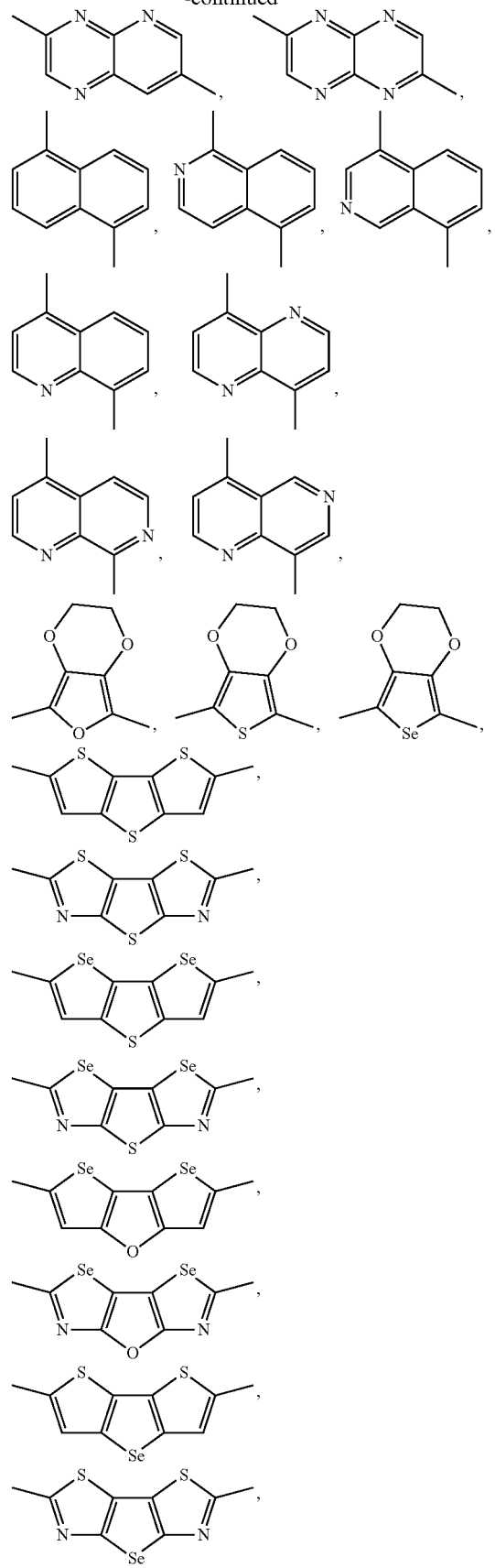

and a combination thereof, which the substitient $R^3$ of the π is selected from the consisting of C1-C30 linear alkyl, C1-C30 branched alkyl, C1-C30 silyl, C1-C30 ester, C1-C30 alkoxy, C1-C30 alkythio, C1-C30 haloalkyl, C1-C30 alkyl substituted with alkene groups or alkyne groups, C1-C30 cyanoalkyl, C1-C30 nitroalkyl C1-C30 hydroxyalkyl, C1-C30 keto-alkyl, halogen, and combination thereof.

Preferably, the EG is selected from the group consisting of

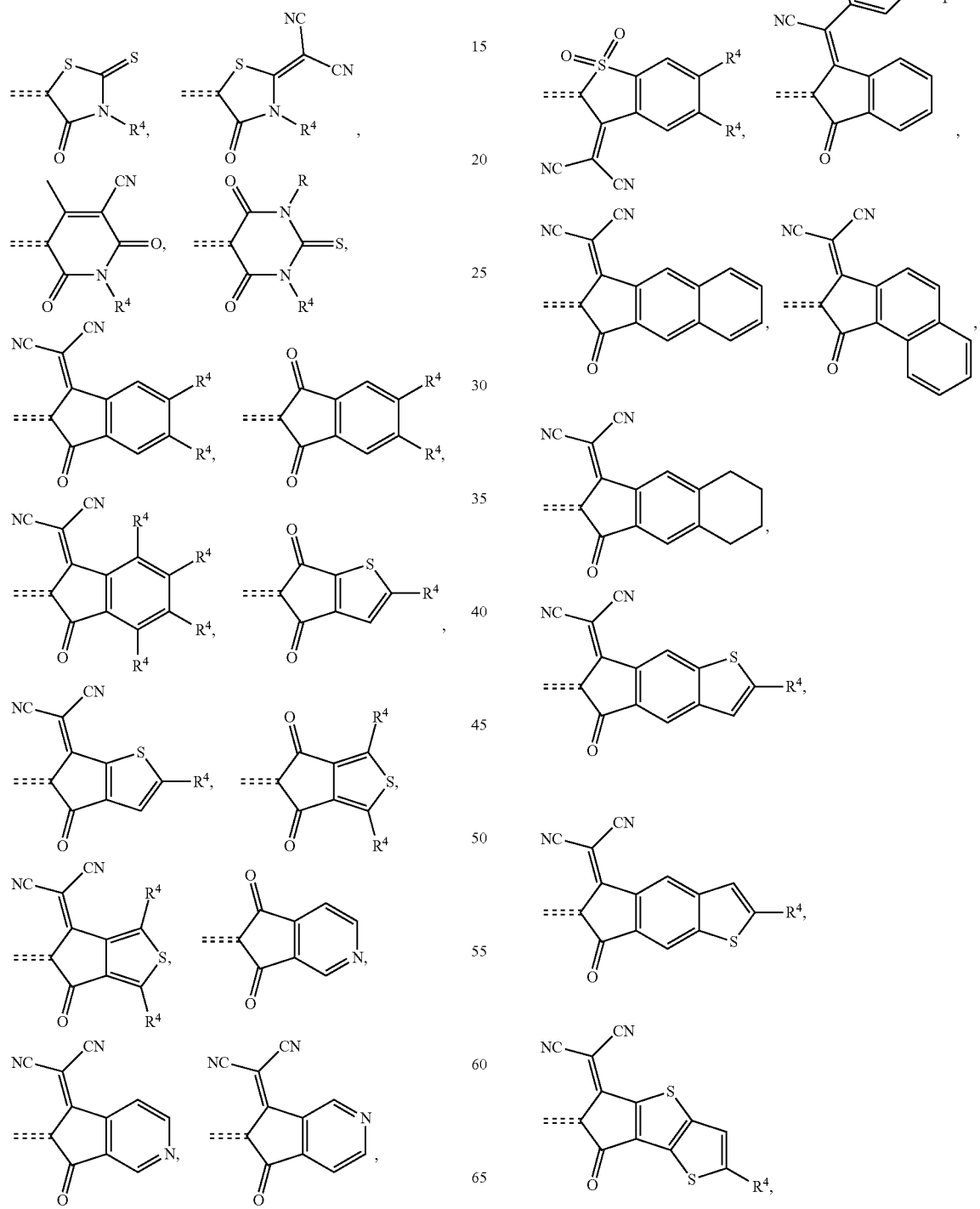

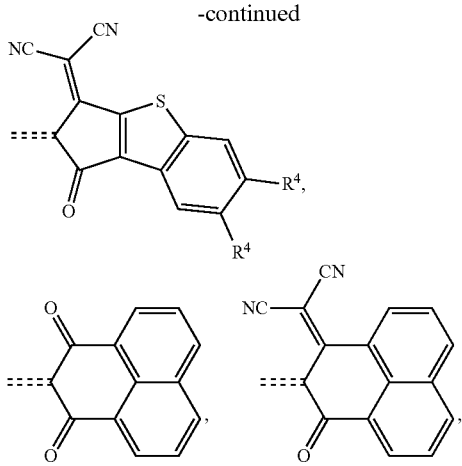

and combination thereof, which the substituent $R^4$ of EG is selected from the group consisting of hydrogen atom, halogen, C1-C20 alkyl, C1-C20 alkoxy, C1-C20 carbonylalkyl, C1-C20 ester, C1-C20 cyanoalkyl, and a combination thereof.

It is another object of the present invention to provide an organic optoelectronic device including the non-fullerene acceptor compounds containing benzoselenadiazole. The organic optoelectronic device includes a substrate, a bottom electrode disposed on the substrate, a top electrode arranged opposite to the bottom electrode, and an intermediate layer mounted between the bottom electrode and the top electrode. The intermediate layer consists of a first carrier transport layer, an active layer, and a second transport layer. The active layer which is arranged between the first carrier transport layer and the second carrier transport layer includes the present non-fullerene acceptor compounds containing benzoselenadiazole.

Preferably, the first carrier transport layer is disposed on the second carrier transport layer.

Preferably, the second carrier transport layer is disposed on the first carrier transport layer.

Preferably, the first carrier transport layer includes molybdenum trioxide ($MoO_3$) or poly(3,4-ethylenedioxythiophene) polystyrene sulfonate (PEDOT:PSS).

Preferably, the second carrier transport layer includes zinc oxide (ZnO) or poly(9,9-bis(3'-(N,N-dimethyl)-N-ethylammoinium-propyl-2,7-fluorene)-alt-2,7-(9,9-dioctylfluorene))dibromide (PFN-Br).

After tests and measurements, the HOMO energy level of the present invention is increased while its LUMO being kept at a certain level, compared with acceptors available now. Thus, the energy gap is reduced and the absorption band is shifted to a longer wavelength region (red-shift). While used in OPD, the present non-fullerene acceptor compounds containing benzoselenadiazole has quite low leakage current, the spectral range suitable for 940 nm, and high external quantum efficiency. While being applied to OPV and used in combination with p-type polymers, the present invention also has good performance in power conversion efficiency.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

Figure 1:
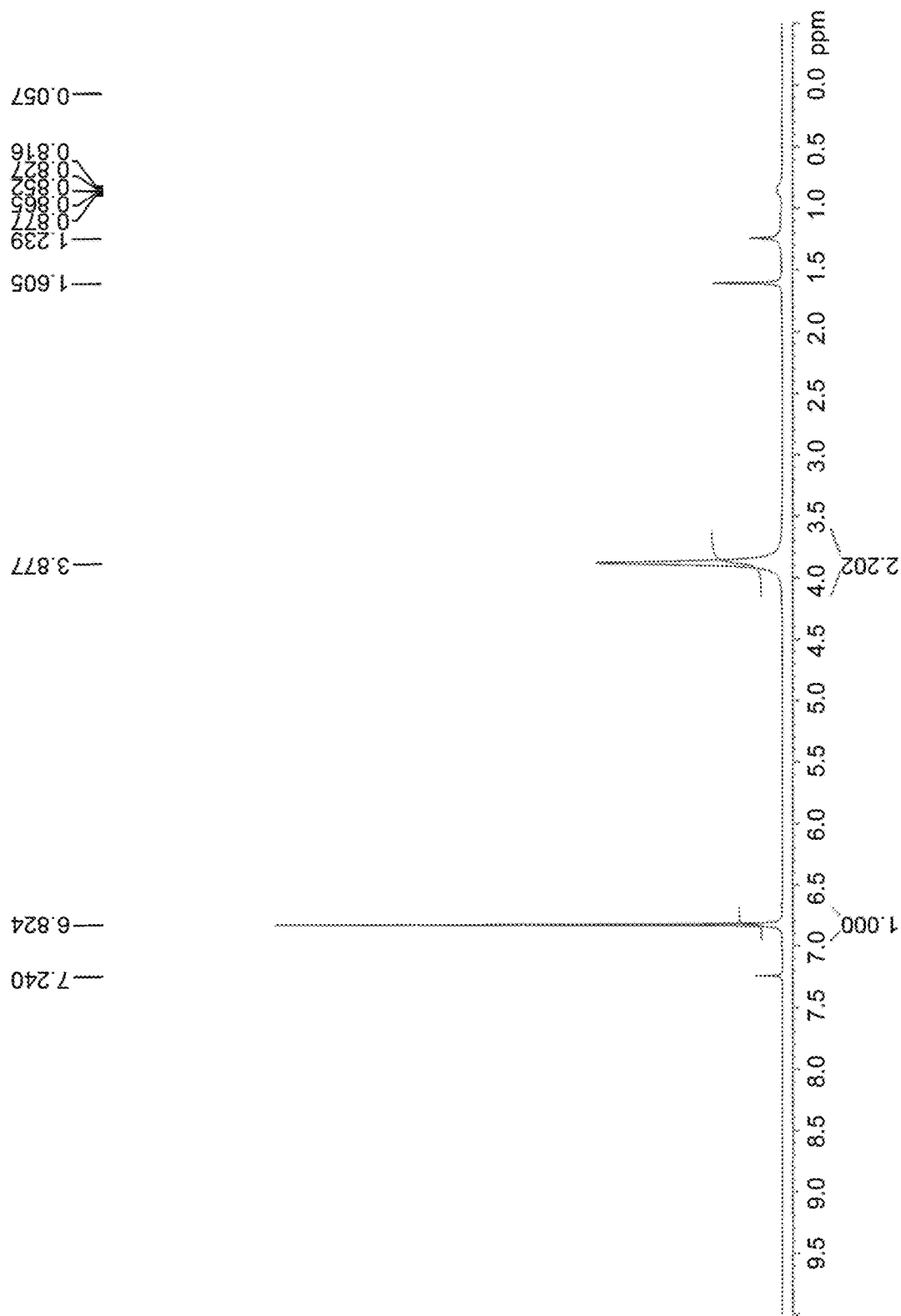
FIG. 1 is a $^1$H NMR (proton nuclear magnetic resonance) spectrum of a compound intermediate M1 of an embodiment according to the present invention.

In order to learn the features and functions of the present invention, please refer to the following embodiments with a detailed description.

The structure of the non-fullerene acceptor compounds containing benzoselenadiazole of the present invention is designed as an A'-D-A-D-A' structure, and the electron-deficient core unit thereof is the polycyclic structure of benzoselenadiazole. The core unit features on that the selenium atom of benzoselenadiazole has a larger atomic radius than the sulfur atom of commonly used benzothiadiazole, so that the intermolecular interaction between two selenium atoms (Se Se) is stronger than that of the sulfur atoms (S S). Thus, the carrier mobility can be increased. Moreover, in the absorption spectrum, the absorption band of the selenium-based non-fullerene materials is shifted to a longer wavelength (red-shift) compared with the absorption band of non-fullerene materials having sulfur atoms so that they have a greater advantage in the production of devices.

Furthermore, non-fullerene materials with selenium atoms have better performance in leakage test than non-fullerene materials having sulfur atoms so that the power conversion efficiency of OPV can be improved.

As the unit arranged at each of two sides of benzoselenadiazole, $Ar^1$ is a monocyclic heterocyclic group which preferably includes sulfur, selenium, oxygen, nitrogen, and tellurium atoms. The unit $Ar^1$ can be connected to different carbon chains on the nitrogen atoms therein so that the solubility of the compound is further increased while oxygen, sulfur, selenium, and tellurium atoms with different electronegativity and atomic radius are related to modulation of molecular energy level, intermolecular interaction, carrier mobility and absorption range.

The unit $Ar^2$ adjacent to the unit $Ar^1$ is a heterocyclic aromatic derivative either monocyclic or polycyclic, and preferably containing sulfur, selenium, oxygen, nitrogen, and tellurium atoms. $Ar^2$ has different combinations of various kinds of atoms and a single ring/or multiple rings. The unit $Ar^2$ is capable of being connected with different carbon chains owing to the nitrogen atom therein so that the solubility of the compound is further increased. Owing to oxygen, sulfur, selenium, and tellurium atoms with different electronegativity and atomic radius, the unit $Ar^2$ has different energy levels and carrier mobility. The unit $Ar^2$ with a single ring has a simpler structure so that fewer functional groups can be modified. Compared with the unit with a single ring, the unit with multiple rings has more positions available for manipulating the molecular structure and this is beneficial to the modification of material properties. The selection of the atoms and the monocyclic/polycyclic ring has a great influence on the energy level, absorption spectrum, and solubility of the material. Along with the increasing numbers of rings, the conjugated length is increased then the molecular energy gap is getting smaller and changing the absorption spectrum.

Used as an acceptor unit in the compound, the unit $\pi$ is a monocyclic or polycyclic derivative. The number of the unit $\pi$ being connected in the structure is preferably from 0 to 5. According to requirements, the unit $\pi$ has different combinations of various kinds of atoms and a single ring/or multiple rings. Owing to the nitrogen atom, the unit $\pi$ is able to be connected with different carbon chains for increasing the solubility of the compound. The oxygen, sulfur, selenium, and tellurium atoms with different electronegativity and atomic radius make the unit $\pi$ have different energy levels, carrier mobility, and absorption range. The unit $\pi$ with a single ring has a simpler structure so that fewer functional groups can be modified while the unit $\pi$ with multiple rings provides more positions for manipulating the molecular structure compared with the single ring and this is beneficial to the modification of material properties. The selection of the atoms and the monocyclic/polycyclic ring has a great influence on the energy level, absorption spectrum, and solubility of the material. Along with the increasing numbers of rings, the conjugated length is increased then the molecular energy gap is getting smaller and changing the absorption spectrum.

The terminal units of the non-fullerene acceptor compound containing benzoselenadiazole are an electron-withdrawing unit, preferably a monocyclic or polycyclic derivative containing at least one ketone and at least one electron-withdrawing group. The unit includes various combinations of different atoms in the form of a monocyclic ring or a polycyclic ring. The materials having an electron-withdrawing group of ketones can increase the intermolecular non-covalent interactions, affect molecular arrangement, and improve carrier mobility. Moreover, along with the increasing strength and amount of the electron-withdrawing unit, the intensity of charge transfer between molecules is significantly increased for further improvement in carrier mobility and material absorption intensity as well as modulation of red-shift in the absorption spectrum. Thereby the non-fullerene acceptor compound has more applications. The options of monocyclic and polycyclic rings provide more positions for modification of functional groups, adjustment of intermolecular interaction, and providing electron-withdrawing effect.

Figure 8:
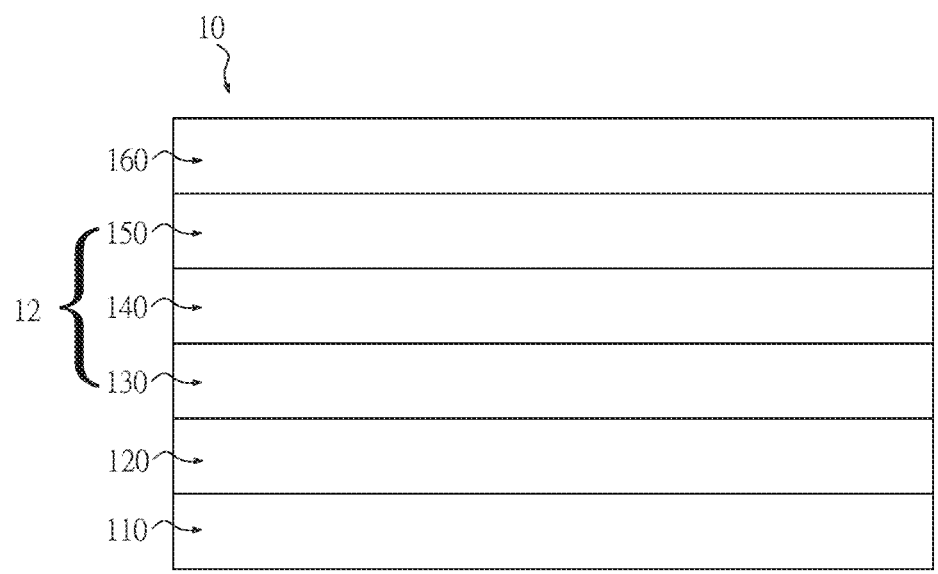
FIG. 8 is a schematic drawing showing the structure of an organic optoelectronic device of an embodiment according to the present invention.
Figure 9:
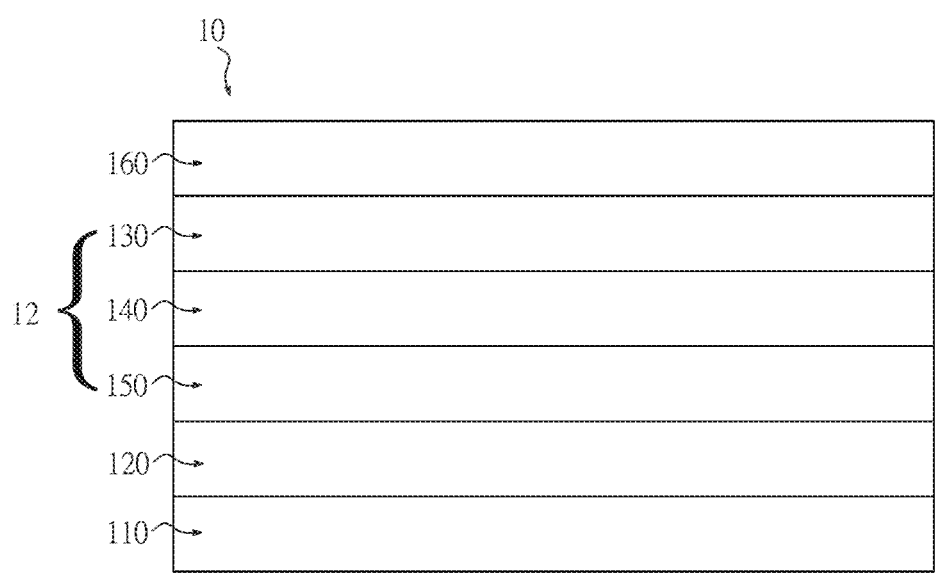
FIG. 9 is a schematic drawing showing another structure of an organic optoelectronic device of an embodiment according to the present invention.

Refer to FIG. 8 and FIG. 9, an organic optoelectronic device 10 (such as organic photodetectors (OPD) and organic photovoltaic (OPV) cells) including non-fullerene acceptor compounds containing benzoselenadiazole according to the present invention includes a substrate 110, a bottom electrode 120, an intermediate layer 12 and a top electrode 160 in turn. The intermediate layer 12 consists of a first carrier transport layer 130, a second transport layer 150, and an active layer 140 which is arranged between the first carrier transport layer 130 and the second carrier transport layer 150 and including the present non-fullerene acceptor compounds containing benzoselenadiazole.

According to the fields being applied, the second carrier transport layer 150, and the first carrier transport layer 130 on two sides of the intermediate layer 12 respectively are interchangeable. That means the first carrier transport layer 130 is disposed on the second carrier transport layer 150 or the second carrier transport layer 150 is disposed on the first carrier transport layer 130.

The substrate 110 of the organic optoelectronic device 10 is made of glass or plastic. The bottom electrode 120 used is a metal conductive layer with high work function and preferably made of indium tin oxide (ITO) or their derivatives while the top electrode 160 is a metal conductive layer with low work function and preferably made of silver, aluminum, or gold.

The first carrier transport layer 130 of the organic optoelectronic device 10 is used for controlling transport of carriers generated after the organic optoelectronic device 10 being exposed to light and made of metal oxides or conductive polymers, preferably molybdenum trioxide ($MoO_3$) or poly(3,4-ethylenedioxythiophene) polystyrene sulfonate (PEDOT:PSS). As to the second carrier transport layer 150, it is also used for controlling transport of carriers generated after the organic optoelectronic device 10 being exposed to light and made of metal oxides or conductive polymers, preferably zinc oxide (ZnO) or poly(9,9-bis(3'-(N,N-dimethyl)-N-ethylammoinium-propyl-2,7-fluorene)-alt-2,7-(9, 9-dioctylfluorene))dibromide (PFN-Br).

A method for preparing the present invention is further described in detail. The following compounds N1-N10 are non-fullerene acceptor compounds containing benzoselenadiazole of the present invention.

Embodiment 1: Preparation of Compounds N1 and N2
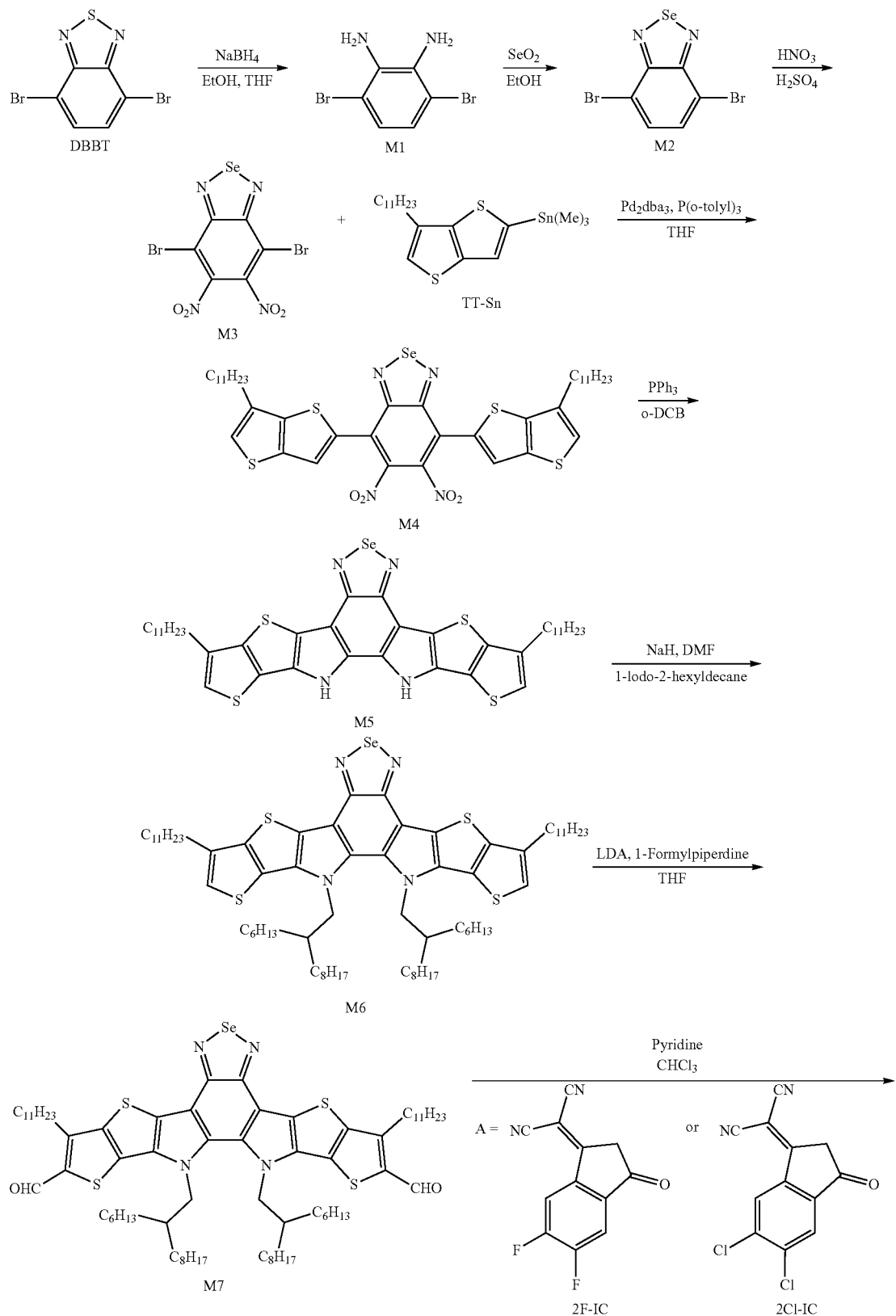

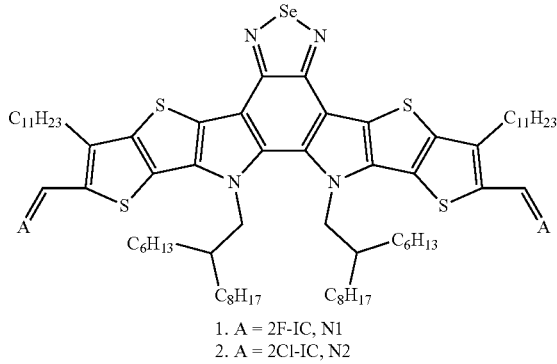

1. A = 2F-IC, N1
2. A = 2Cl-IC, N2

Synthesis of Compounds M1-M7 a. Synthesis of Compound M1

Put 8 g (27.2 mmol) 4,7-Dibromo-2,1,3-benzothiadiazole (DBBT) into a 500 ml three-necked bottle. Add 120 mL ethanol and 200 mL tetrahydrofuran (THF) into the bottle and stir the solution with a stir bar in the ice bath until DBBT is completely dissolved. Slowly add 21 g (544 mmol) sodium borohydride ($NaBH_4$) into the solution and allow the solution to stir in the ice bath for 30 minutes. Then remove the ice bath and react at room temperature for 1 hour. A crude product is acidified and extracted three times with ethyl acetate/$H_2O$. The organic layer is collected and dried with magnesium sulfate ($MgSO_4$). Next, the solvent is removed to get white solid product M1 (6.5 g, 90%). Analytical data for M1: $^1H$ NMR (500 MHz, $CDCl_3$): δ 6.82 (s, 2H), 3.88 (s, 4H), as shown in FIG. 1.

b. Synthesis of Compound M2

Figure 2:
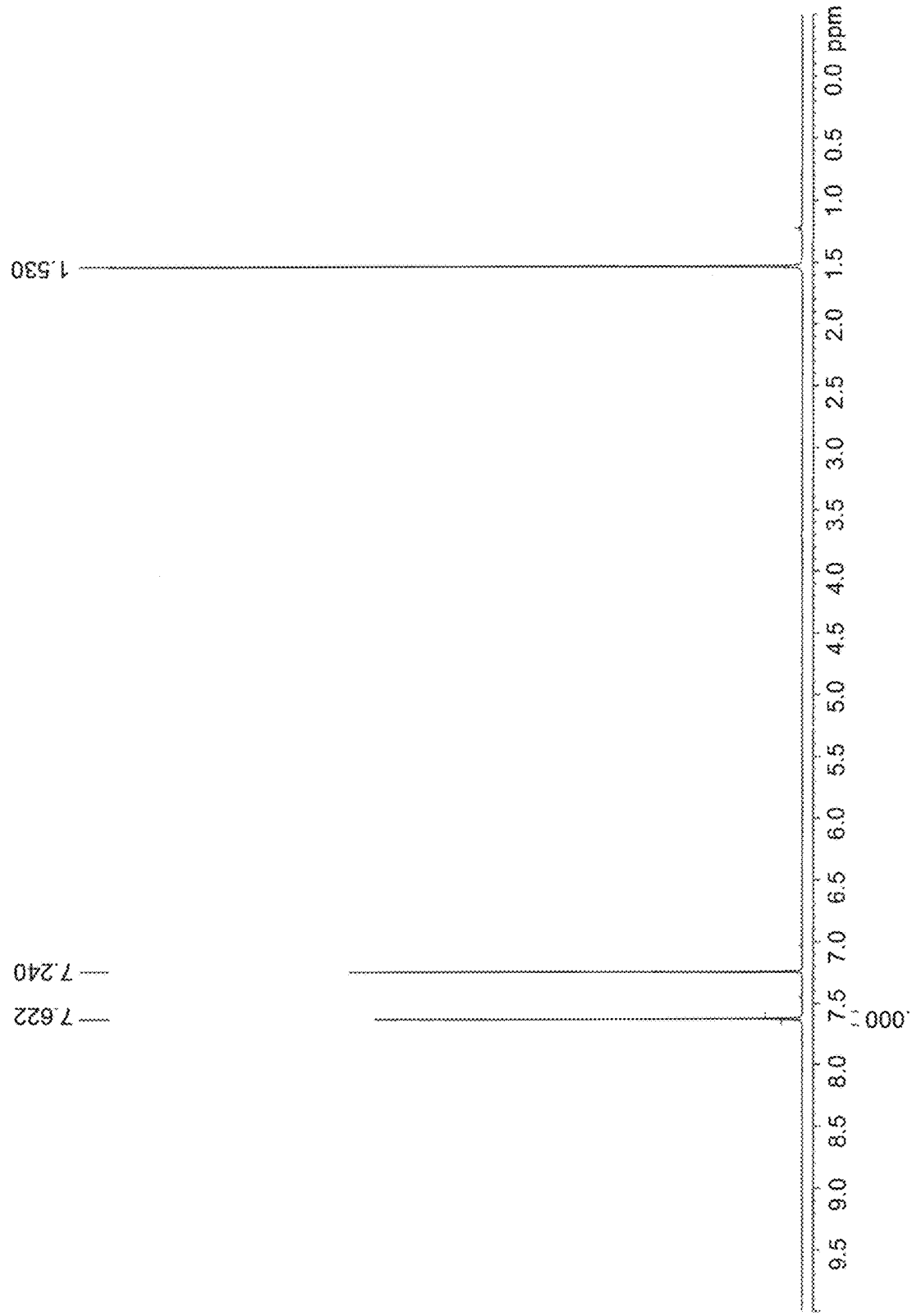
FIG. 2 is a $^1$H NMR spectrum of a compound intermediate M2 of an embodiment according to the present invention.

7 g Compound M1 (26.3 mmol) and 3.5 g selenium dioxide ($SeO_2$) (31.6 mmol) are weighted and placed into a 500 mL three-necked bottle. Add 210 mL ethanol into the bottle, stir with the stir bar and heat to 75 degrees Celsius (° C.) and reflux for 1 hour. Then place the reaction bottle into an ice bath to get a resulting white solid precipitate upon cooling. The white solid is treated by vacuum filtration and washed with ethanol (EtOH) to get a white solid product M2 (8 g, 90%). Analytical data for M2: $^1H$ NMR (500 MHz, $CDCl_3$): δ 7.62 (s, 2H), as shown in FIG. 2.

c. Synthesis of Compound M3 Prepare a 250 mL three-necked bottle with a stir bar stirred therein. Add 42 mL sulfuric acid ($H_2SO_4$), 14 mL fuming $H_2SO_4$, and 35 mL fuming $HNO_3$ into the 250 mL three-necked bottle with a stir bar in the ice bath. Then add 6.5 g compound M2 (18.1 mmol) into the bottle, introduce nitrogen gas, and react for 18 hours while the mixture was slowly warmed to room temperature. After completion of the reaction, the reactant solution is poured into ice, treated by vacuum filtration after the ice is melted, and rinsed with water. The yellowish-brown solid product M3 (3.5 g, 43%) is then collected. Since compound M3 doesn't include hydrogen atoms, no proton spectrum identification is performed.

d. Synthesis of Compound M4

Figure 3:
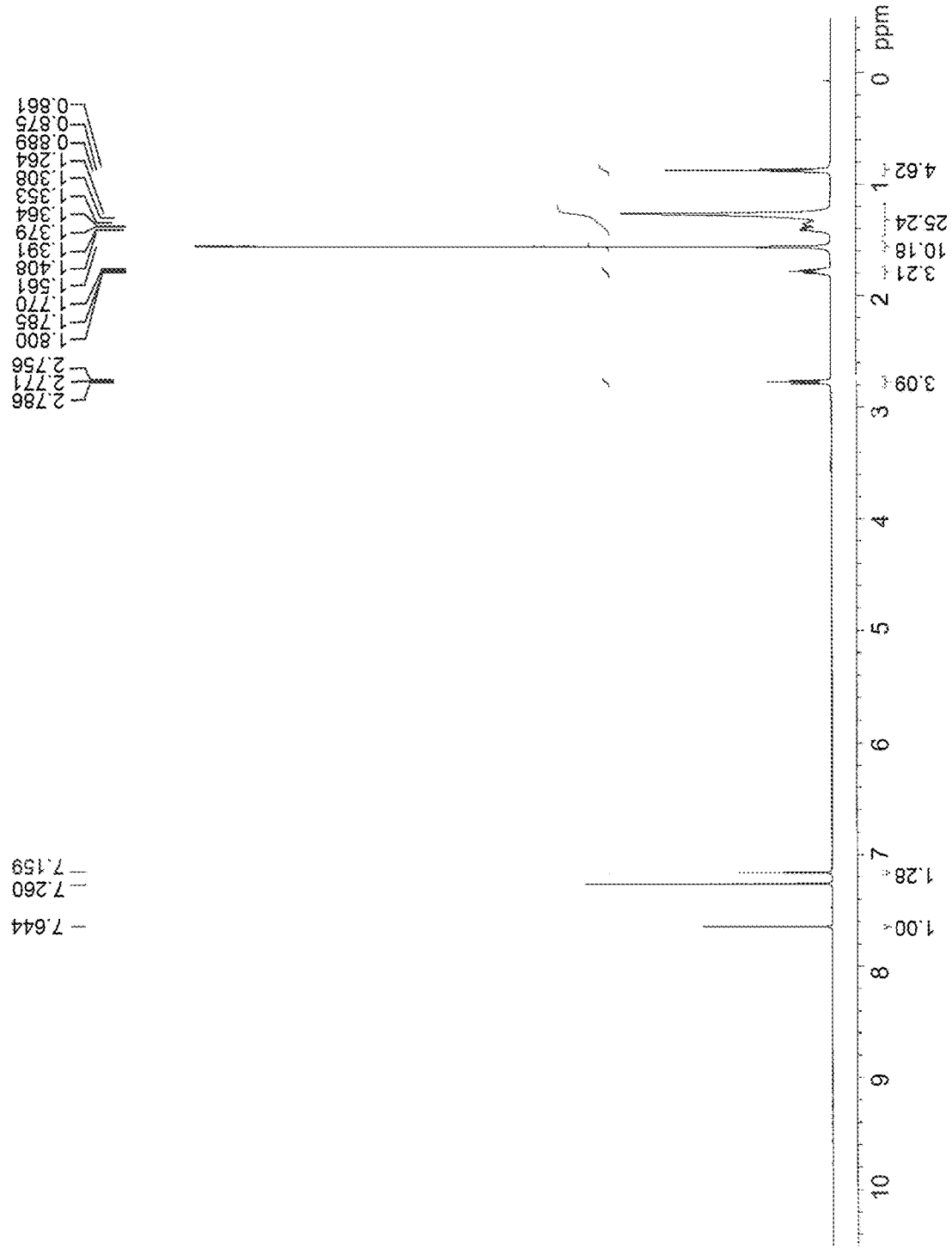
FIG. 3 is a $^1$H NMR spectrum of a compound intermediate M4 of an embodiment according to the present invention.

Add 3.5 g (8.1 mmol) compound M3 and 8.9 g (17.9 mmol)) trimethyl-(3-undecylthieno[3,2-b]thiophen-5-yl)stannane (TT-Sn) into a 250 mL three-necked bottle. Then add 105 mL THF into the solution, stir the solution with a stir bar and purge with argon at room temperature for 30 minutes to remove oxygen. In the argon system, add 298 mg (0.33 mmol) tris(dibenzylideneacetone)dipalladium ($Pd_2dba_3$) and 396 mg (1.30 mmol) tris(o-tolyl)phosphine ($P(o-tolyl)_3$ into the solution and heat to 70° C. and reflux for 2 hours. Then purify the products and remove catalyst by silica gel and celite columns and dry the solvent under vacuum. Add THF and heptane, stir for dissolution, and add drops of methanol for recrystallization. Vacuum filtration is used to collect the desired solid and get red solid product M4 (4.9 g, 70%). Analytical data for M4: $^1H$ NMR (500 MHz, $CDCl_3$): δ 7.64 (s, 2H), 7.16 (s, 2H), 2.77 (t, J=7.5 Hz, 4H), 1.80-1.77 (m, 4H), 1.41-1.26 (m, 32H), 0.88 (t, J=7.0 Hz 6H), as shown in FIG. 3.

e. Synthesis of Compound M5

Place 6 g (8.0 mmol) M4 and 21 g (80.4 mmol) triphenyphospilne ($PPh_3$) into a 500 mL three-necked bottle and add 173 mL ortho-dichlorobenzene (o-DCB) into the bottle. Purge the solution with argon at room temperature for 30 minutes for the removal of oxygen. Heat the solution to 180° C. and reflux for 22 hours. After the reaction is completed, the reacted mixture was cool down to room temperature and then added methanol for precipitation. Stir the cloudy liquid obtained for 30 minutes and use vacuum filtration to collect the solid. The solid is passed through a short column of silica gel and less polar impurities are removed by using DCM/Heptane=1/1 as eluent. Then extract the product by washing with THF and dry the solvent under vacuum to get brown solid product M5 (3.3 g, 64%). Owing to the poor solubility of compound M5, $^1H$ NMR identification for compound M5 is not performed.

f. Synthesis of Compound M6

Figure 4:
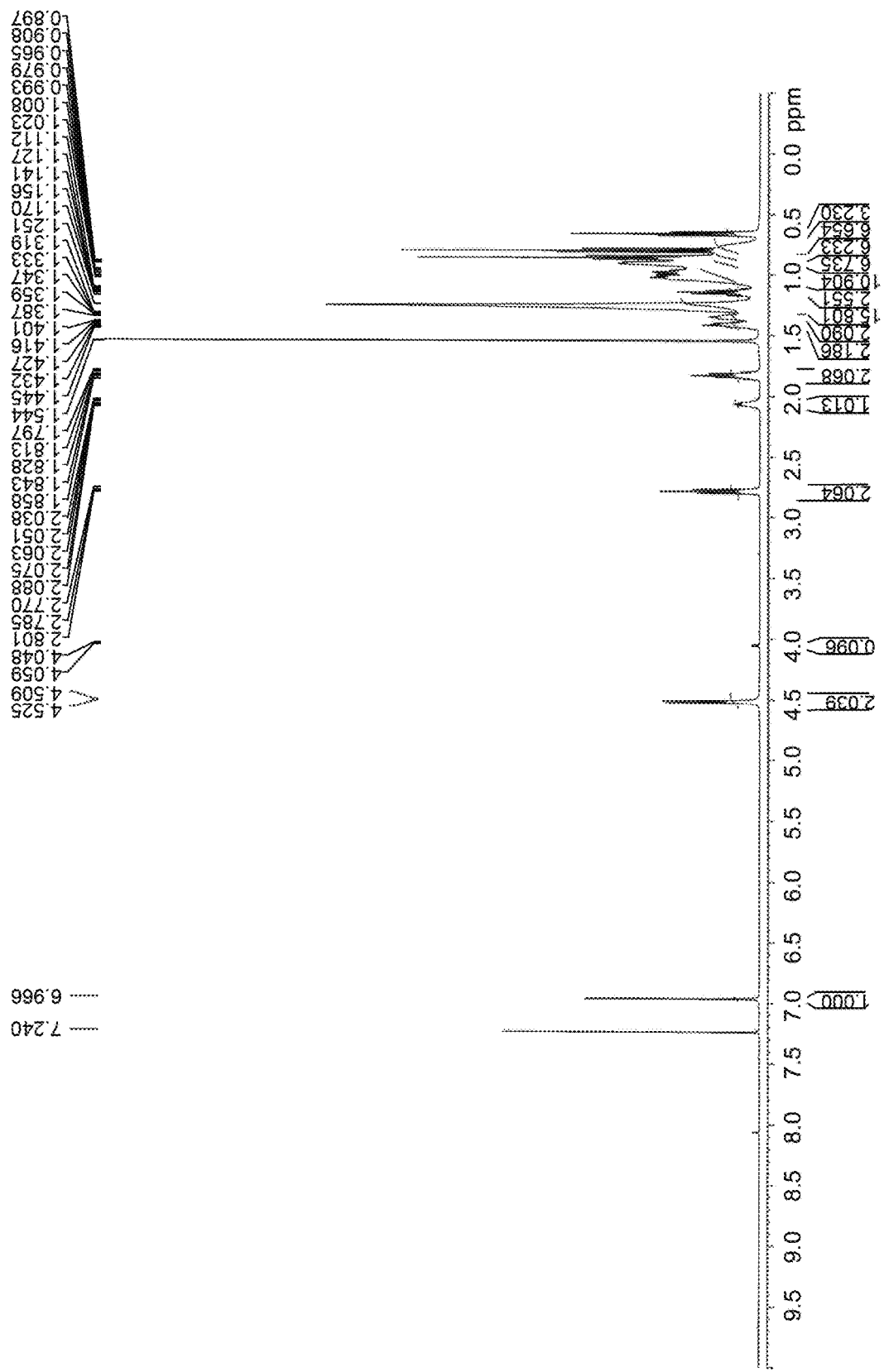
FIG. 4 is a $^1$H NMR spectrum of a compound intermediate M6 of an embodiment according to the present invention.

Add 4.1 g (8.0 mmol) compound M5 and 2.6 g (64.2 mmol) 60% sodium hydride (NaH) into a 250 mL three-necked bottle. Inject 123 mL dry DMF into the bottle and then stir the solution with a stir bar at room temperature for 30 minutes. Add 25.5 g (72.3 mmol) 1-iodo-2-hexyldecane at room temperature and heat under reflux at 80° C. for 5 hours. Next, water is slowly added for stopping the reaction until no more bubbles are generated in the bottle. Extract the solution three times with ethyl acetate/$H_2O$ and separate the organic layer. Add magnesium sulfate ($MgSO_4$) to remove water then the filtrate was removed under vacuum. A red solid product M6 (4.5 g, 70%) is isolated by silica gel column chromatography (with eluent heptane/dichloromethane=5/1). Analytical data for M6: $^1H$ NMR (500 MHz, $CDCl_3$): δ 6.97 (s, 2H), 4.52 (d, J=8.0 Hz, 4H), 2.79 (t, J=7.8 Hz, 4H), 2.09-2.04 (m, 2H), 1.83 (p, J=7.6 Hz, 4H), 1.45-0.79 (m, 92H), 0.66 (d, J=7.0 Hz, 6H), as shown in FIG. 4.

g. Synthesis of Compound M7

Figure 5:
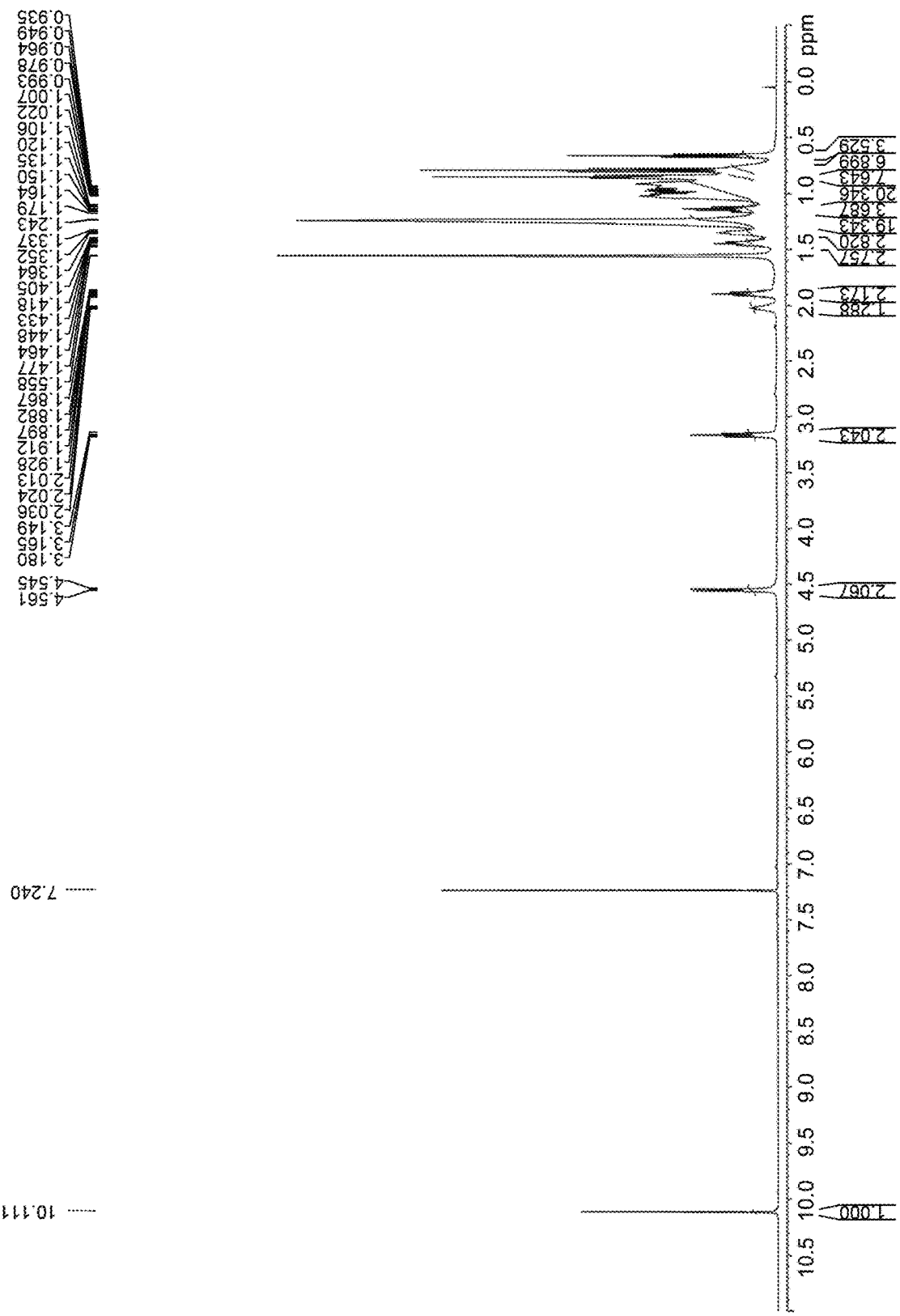
FIG. 5 is a $^1$H NMR spectrum of a compound intermediate M7 of an embodiment according to the present invention.

Add 800 mg (0.64 mmol) compound M6 and inject 32 mL (40 V) dry DMF into the 100 mL three-necked bottle, and stir the solution with a stir bar in ice bath. Then add 2.6 mL (5.15 mmol) lithium diisopropylamide (LDA) slowly into the solution in the ice bath and react for 30 minutes. Next, add 0.71 mL (6.44 mmol) 1-formylpiperidine slowly into the solution in the ice bath and remove the ice bath after completing the addition. Warm the solution to room temperature and react for 30 minutes. Slowly add methanol (MeOH) into the solution to stop the reaction until no more bubbles are generated. Perform extraction three times with ethyl acetate/$H_2O$ and separate the organic layer. Add magnesium sulfate ($MgSO_4$) for removal of water then the filtrate was removed under vacuum. A red oily product M7 (470 mg, 60%) is obtained by Silica Gel column chromatography (with eluent heptane/dichloromethane=1/1). Analytical data for compound M7: $^1$H NMR (500 MHz, $CDCl_3$): δ 10.11 (s, 2H), 4.55 (d, J=8.0 Hz, 4H), 3.17 (t, J=7.8 Hz, 4H), 2.04-2.01 (m, 2H), 1.90 (p, J=7.6 Hz, 4H), 1.48-0.78 (m, 92H), 0.66 (d, J=7.0 Hz, 6H), as shown in FIG. 5.

h. Preparation of Compound N1

Figure 6:
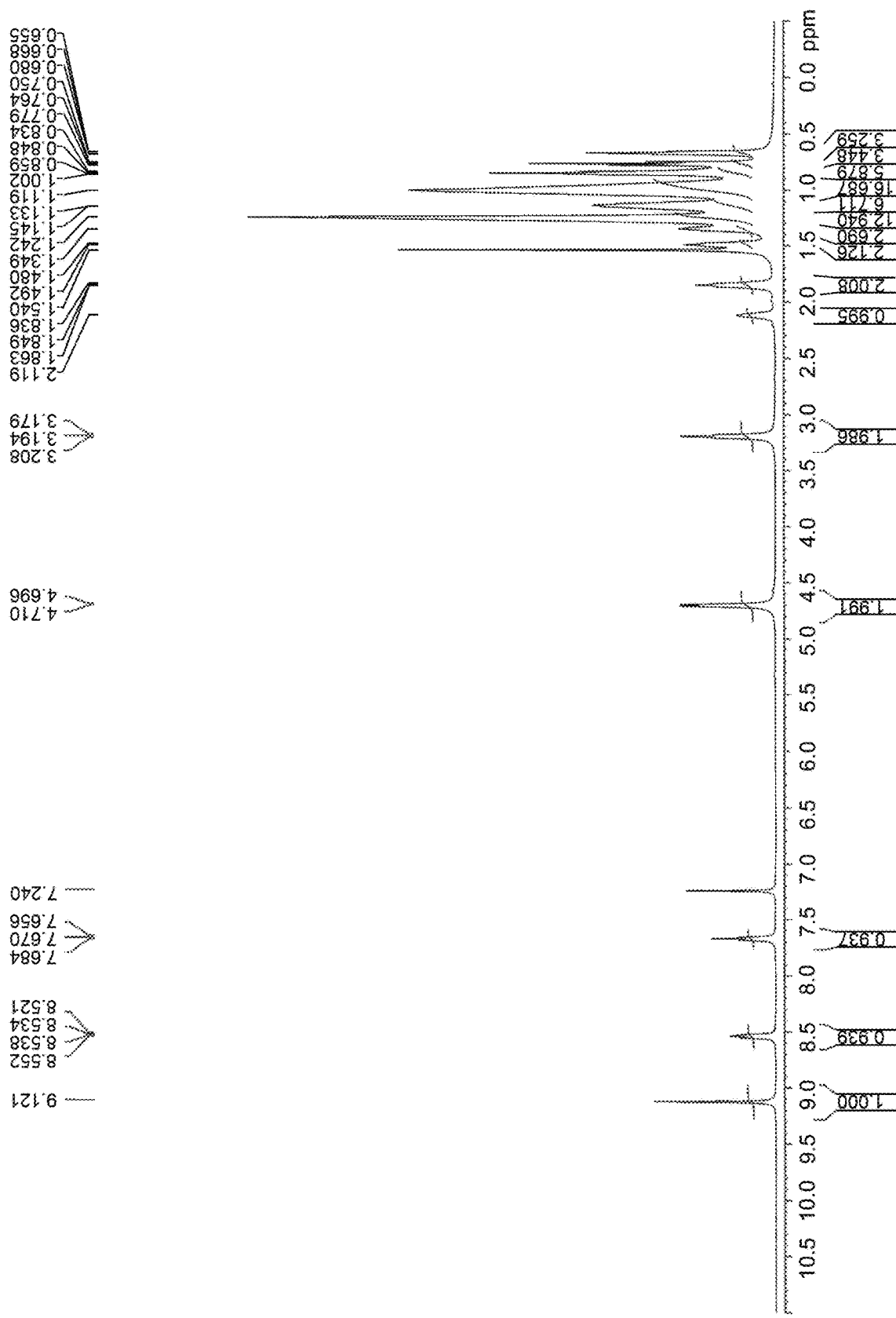
FIG. 6 is a $^1$H NMR spectrum of a compound intermediate N1 of an embodiment according to the present invention.

Add 510 mg (0.39 mmol) compound M7, 452 mg (1.96 mmol) 2-(5,6-difluoro-3-oxo-2,3-dihydro-1H-inden-1-ylidene)malononitrile, and 15 mL chloroform into a 100 mL three-necked bottle. Stir the solution with a stir bar and purge with argon for 30 minutes to remove oxygen. Then add 0.5 mL pyridine into the solution and heat under reflux at 60° C. for 30 minutes. When the reaction is completed, the mixture was cooled to room temperature and then dry the solvent under vacuum. Wash the crude product with MeOH for one time and acetone for two times respectively with a sonicator. After vacuum filtration, collect the solid and get dark blue solid N1 (406 mg, 60%). Analytical data for dark blue compound N1: $^1$H NMR (500 MHz, $CDCl_3$): 9.12 (s, 2H), 8.55-8.52 (m, 2H), 7.68-7.66 (m, 2H), 4.70 (d, J=7.0 Hz, 4H), 3.19 (t, J=7.3 Hz, 4H), 2.21-2.17 (m, 2H), 1.85 (p, J=6.8 Hz, 4H), 1.49-0.75 (m, 92H), 0.68 (d, J=6.3 Hz, 6H), as shown in FIG. 6.

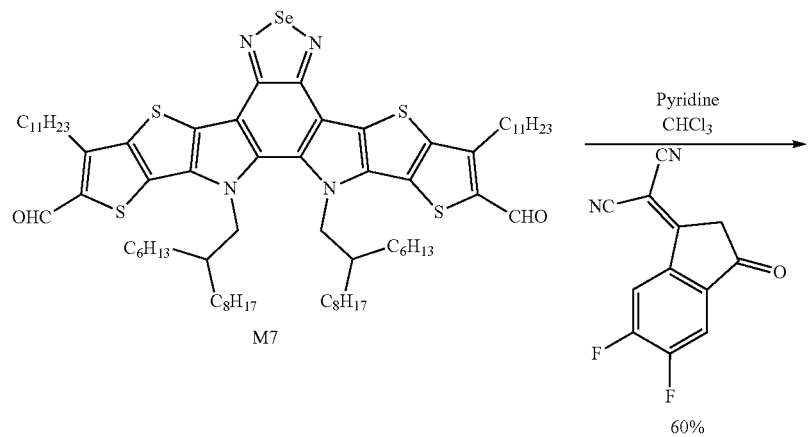

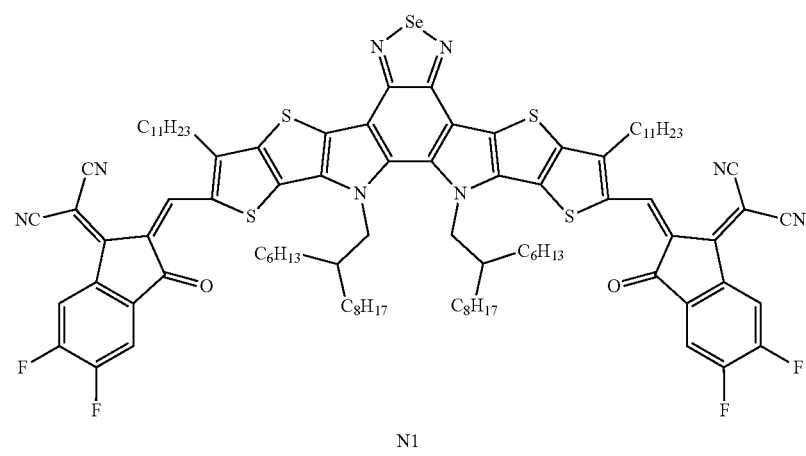

Preparation of Compound N2

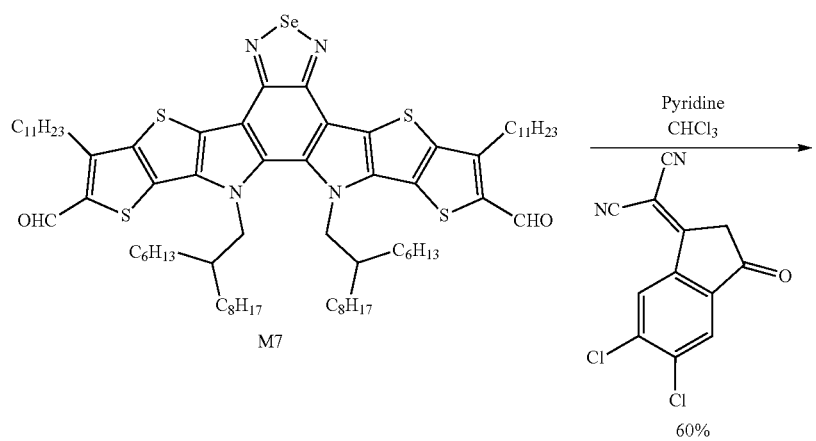

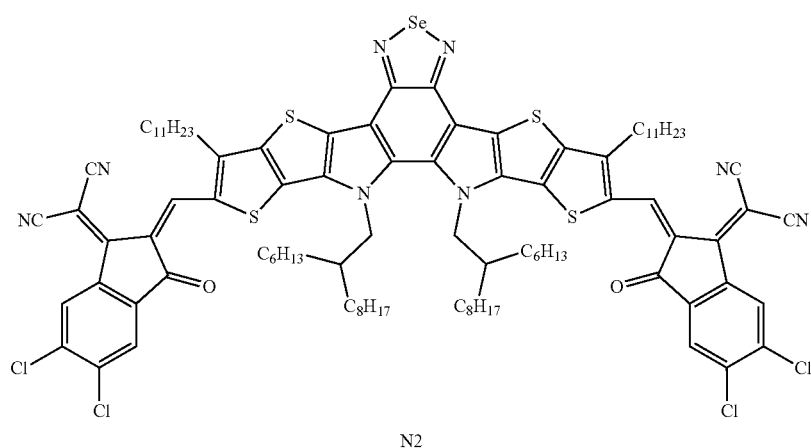

Figure 7:
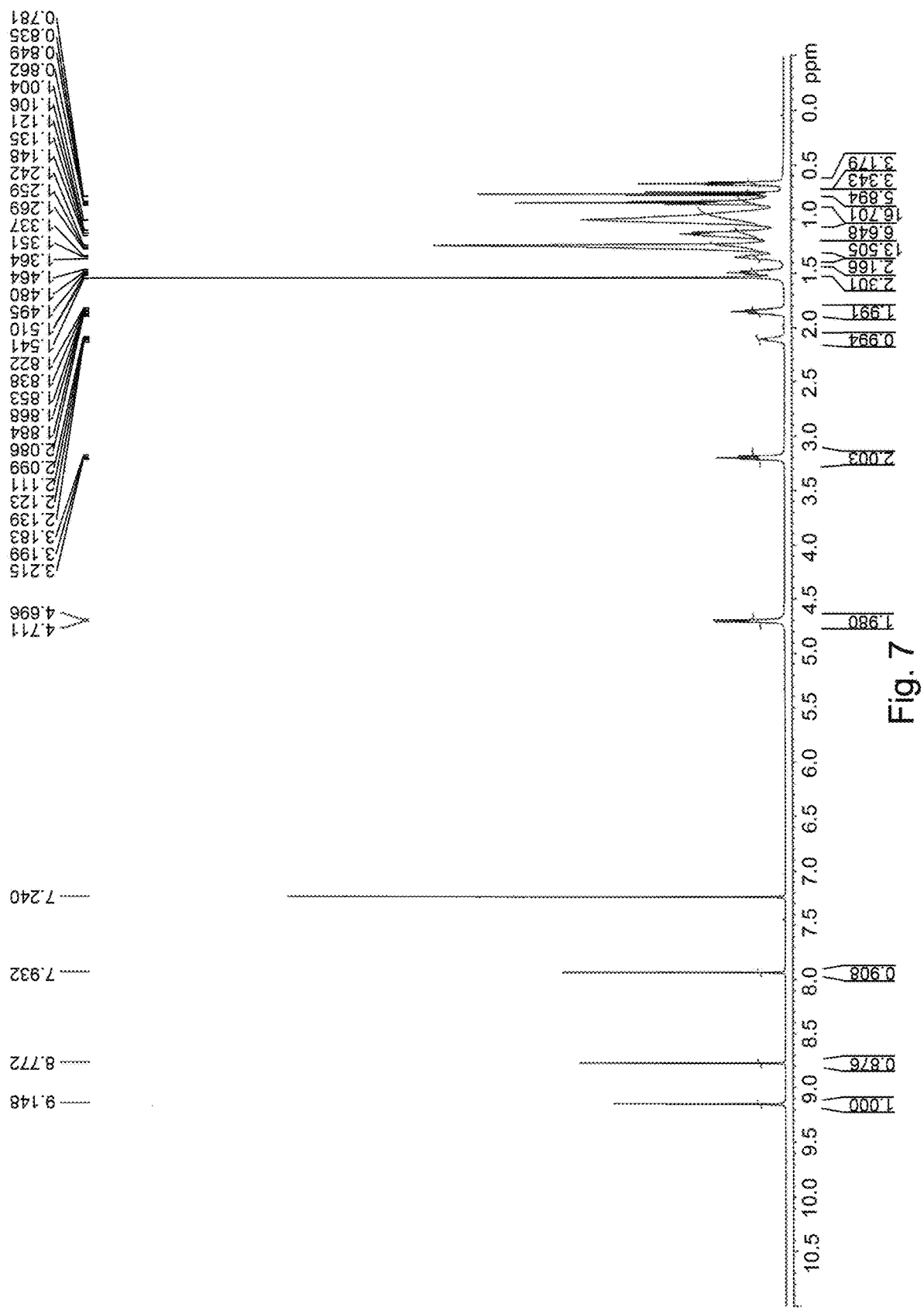
FIG. 7 is a $^1$H NMR spectrum of a compound intermediate N2 of an embodiment according to the present invention.

Add 510 mg (0.39 mmol) compound M7, 515 mg (1.96 mmol) 2-(5,6-dichloro-3-oxo-2,3-dihydro-1H-inden-1-ylidene)malononitrile, and 15 mL chloroform into a 100 mL three-necked bottle. Stir the solution with a stir bar and purge with argon for 30 minutes to remove oxygen. Then add 0.5 mL pyridine into the solution and heat under reflux at 60° C. for 30 minutes. When the reaction is completed, the mixture was cooled to room temperature and dry the solvent under vacuum. Wash the crude product with MeOH for one time and acetone for two times respectively with a sonicator. After vacuum filtration, collect the solid and get dark blue solid N2 (421 mg, 60%). Analytical data for dark blue compound N2: $^1$H NMR (500 MHz, CDCl$_3$): δ 9.15 (s, 2H), 8.77 (s, 4H), 7.93 (s, 2H), 4.70 (d, J=7.5 Hz, 4H), 3.20 (t, J=8 Hz, 4H), 2.14-2.09 (m, 2H), 1.85 (p, J=7.8 Hz, 4H), 1.51-0.75 (m, 92H), 0.67 (d, J=6.8 Hz, 6H), as shown in FIG. 7.

Embodiment 2: Preparation of Compound N3 and Compound N4

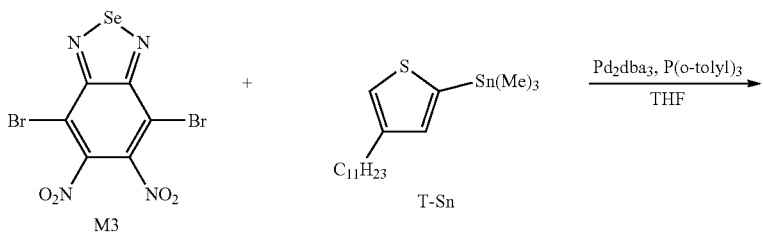

-continued
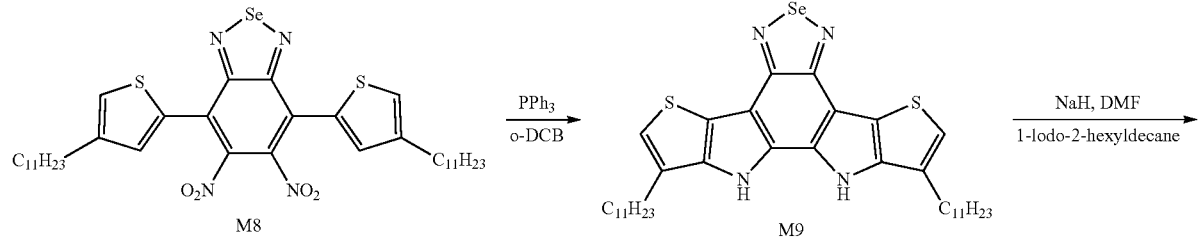
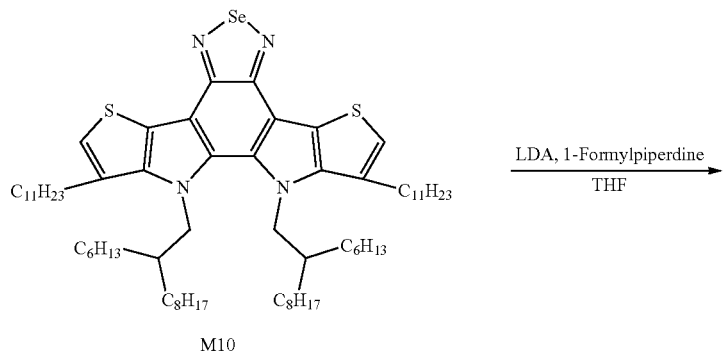
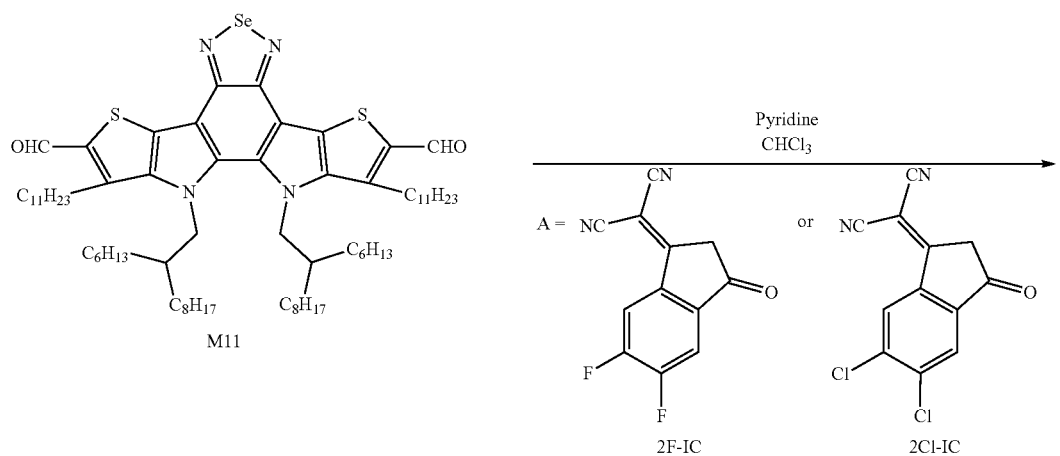
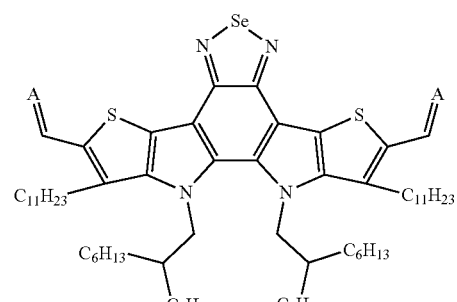
1. A = 2F-IC, N3
2. A = 2Cl-IC, N4

Embodiment 3: Preparation of Compound N5 and Compound N6
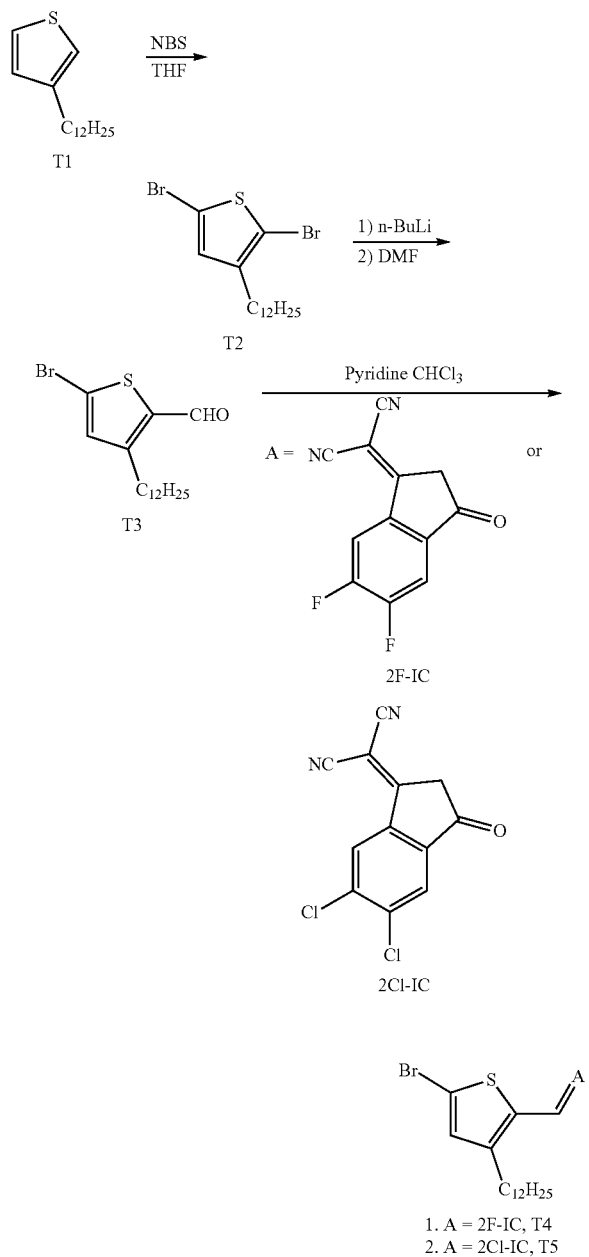
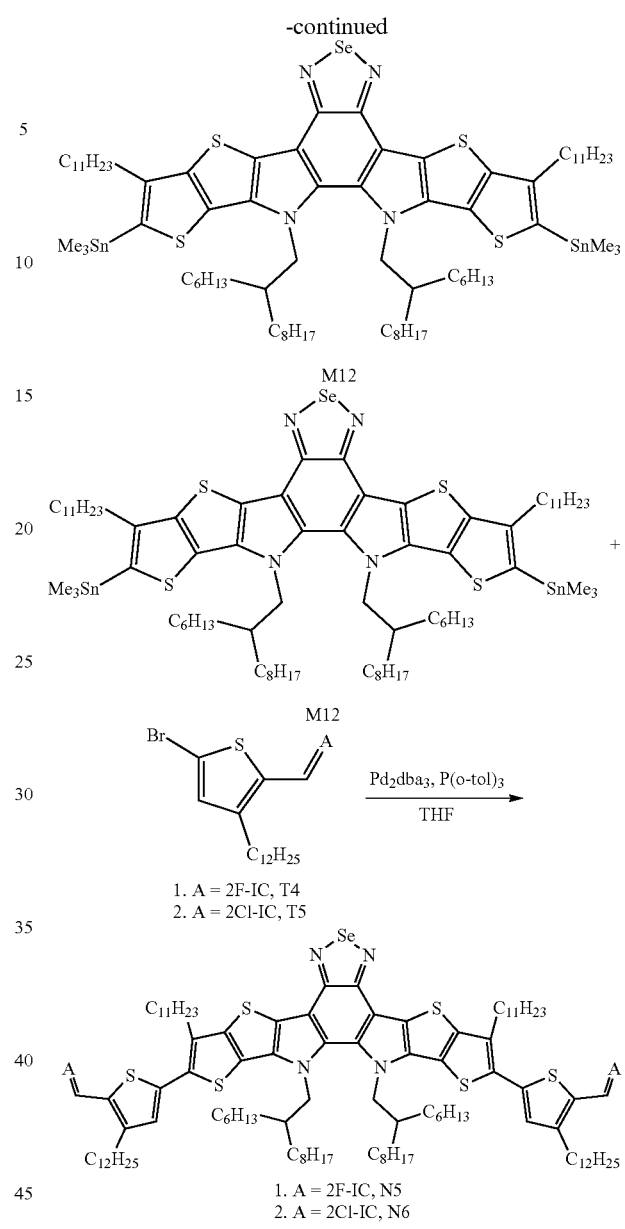
Embodiment 4: Preparation of Compound N7 and Compound N8
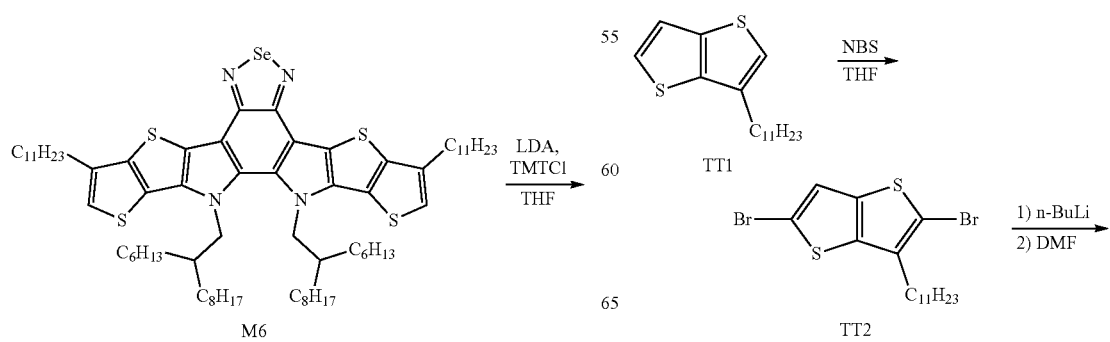

-continued
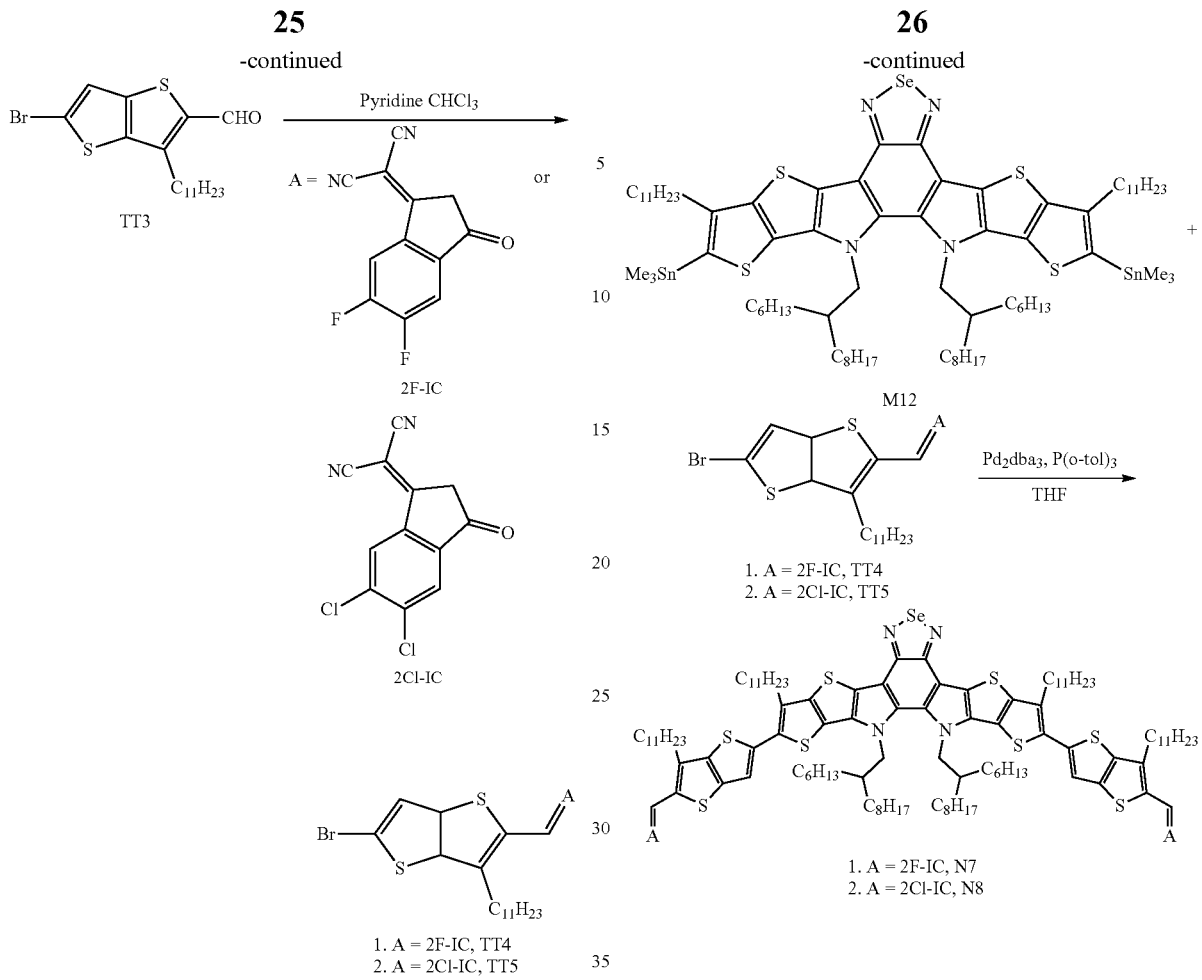
Embodiment 5: Preparation of Compound N9 and Compound N10
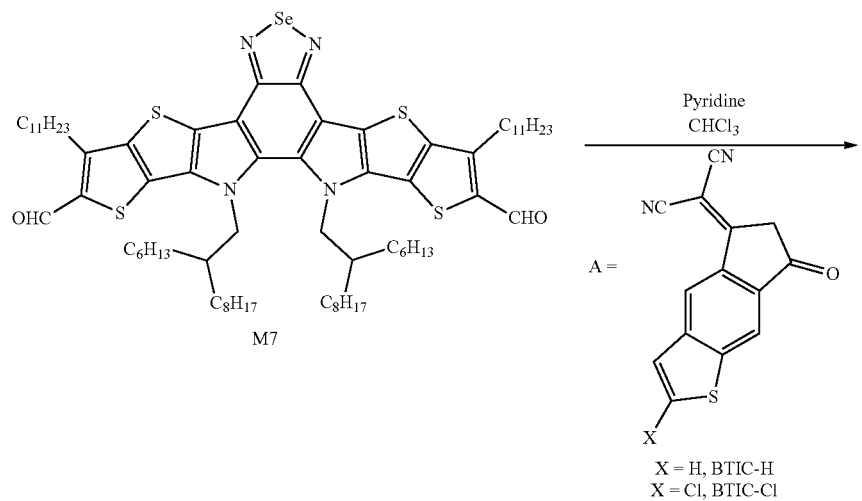

-continued

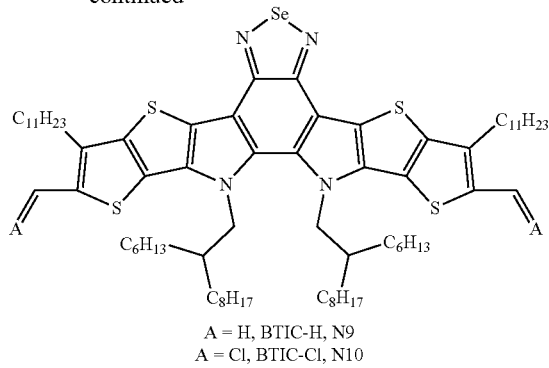

A = H, BTIC-H, N9
A = Cl, BTIC-Cl, N10

In the following embodiments, organic photodetectors (OPD) and organic photovoltaic (OPV) cells are used as examples of the present organic optoelectronic device, and their performance test results are also described.

Embodiment 6: Performance Test-UV Absorption Spectrum of the Material

UV absorption: use ultraviolet (UV)/visible spectrophotometer to acquire an absorbance spectrum of the sample measured. For measurement in solution form, the sample is dissolved with chloroform before the measurement. For measurement in solid form, the sample is prepared into a thin film. The method for preparing the thin film is as follows: the sample concentration is 5 wt % and glass is the base material. The sample is coated on the glass by spin coating and then the measurement of the solid sample is carried out.

Energy level measured by cyclic voltammetry: Cyclic voltammetry is performed on an electrochemical analyzer to investigate the redox behavior of the sample and determine its HOMO and LUMO energy levels. Add 0.1 M tetra-1-butylammonium hexafluorophosphate (Bu$_4$NPF$_6$) acetonitrile solution used as electrolyte solution. Add 0.01 M silver nitrate solution (AgNO$_3$) and 0.1 M TBAP (tetrabutylammonium perchlorate) acetonitrile solution into an Ag/AgCl reference electrode. Pt wire is used as the counter electrode, and the glass carbon electrode is the working electrode. Dissolve the analyte with chloroform and drop the solution to the working electrode to form a film. With the scan rate of 50 mV/sec, the current is measured and plotted against the potential to obtain the cyclic voltammogram of the analyte. The oxidation and reduction potentials of the analyte can be found by the analysis of the cyclic voltammogram. The potential of the reference electrode can be internally calibrated by using the ferrocene/ferrocenium redox couple (Fc/Fc$^+$). The HOMO and LUMO energy levels are estimated using the following equations:

$$\text{HOMO} = -(4.71 \text{ eV} + (E_{ox} - E_{ref}))$$

$$\text{LUMO} = \text{HOMO} + E_g^{opt}$$

Figure 10:
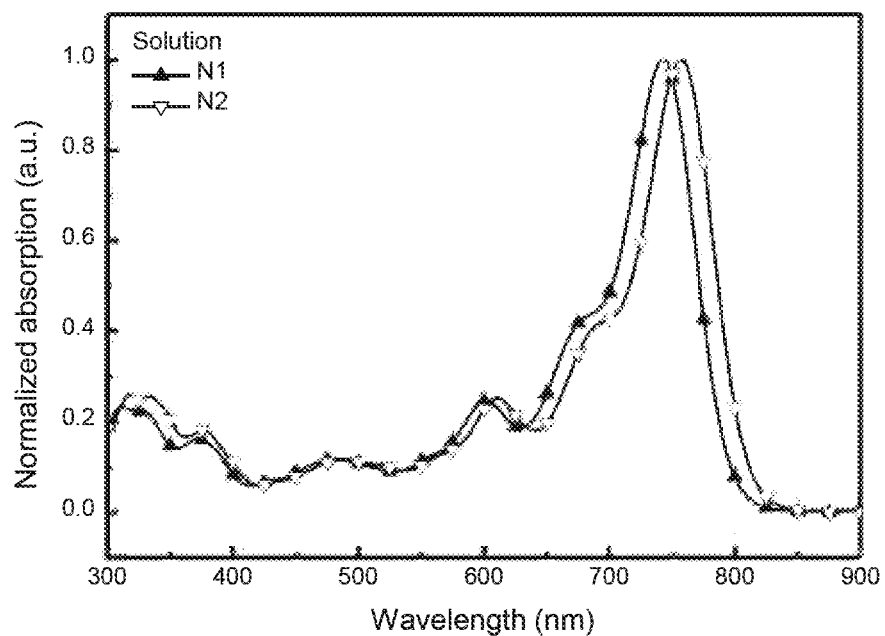
FIG. 10 shows optical absorption spectra for compound N1 and compound N2 in solution according to the present invention.
Figure 11:
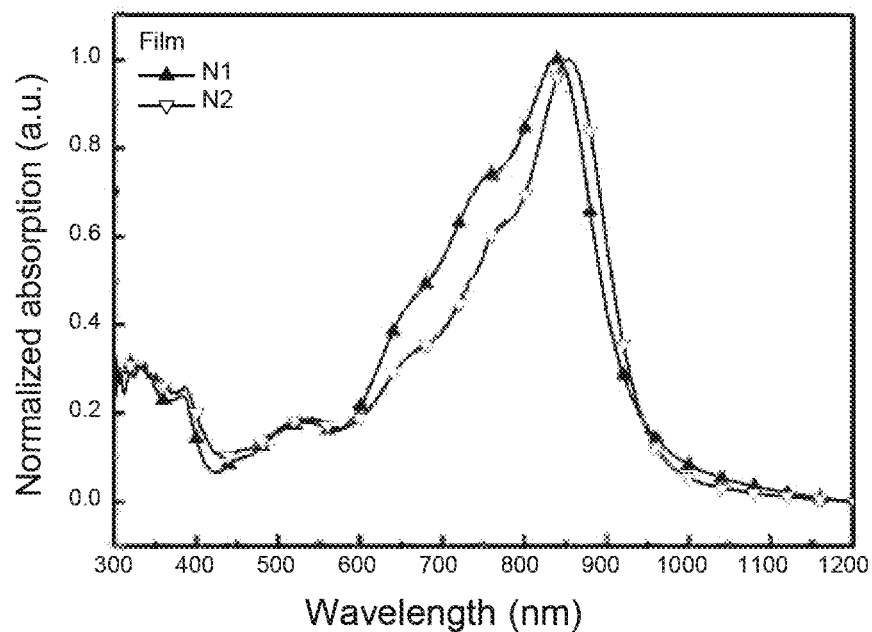
FIG. 11 shows optical absorption spectra for compound N1 and compound N2 in thin films according to the present invention.
Figure 12:
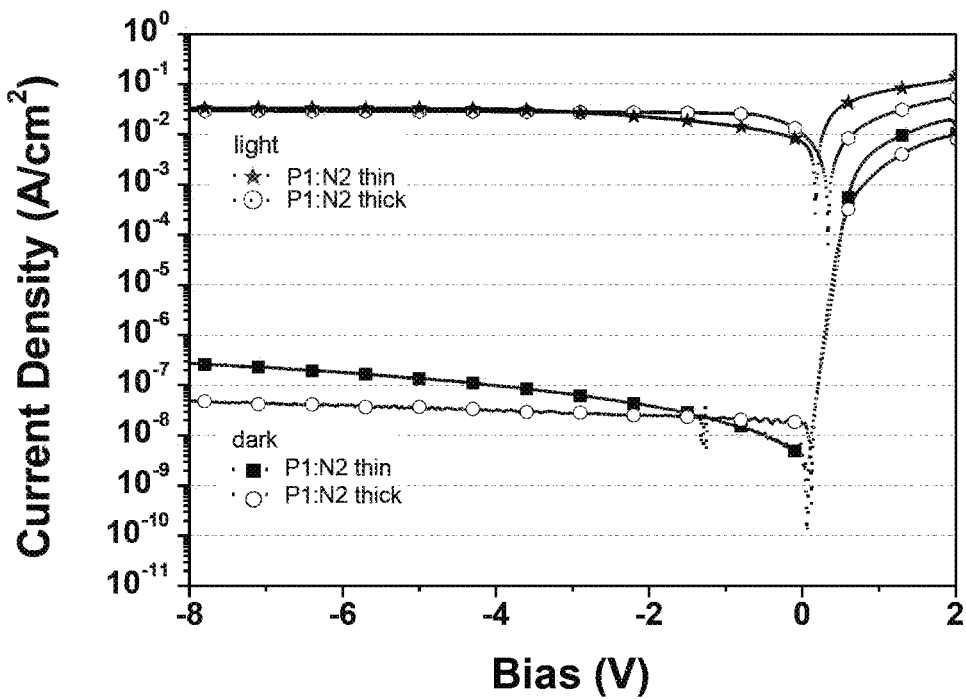
FIG. 12 shows current density versus bias voltage curves of organic photodetectors (OPD) of an embodiment according to the present invention.
Figure 13:
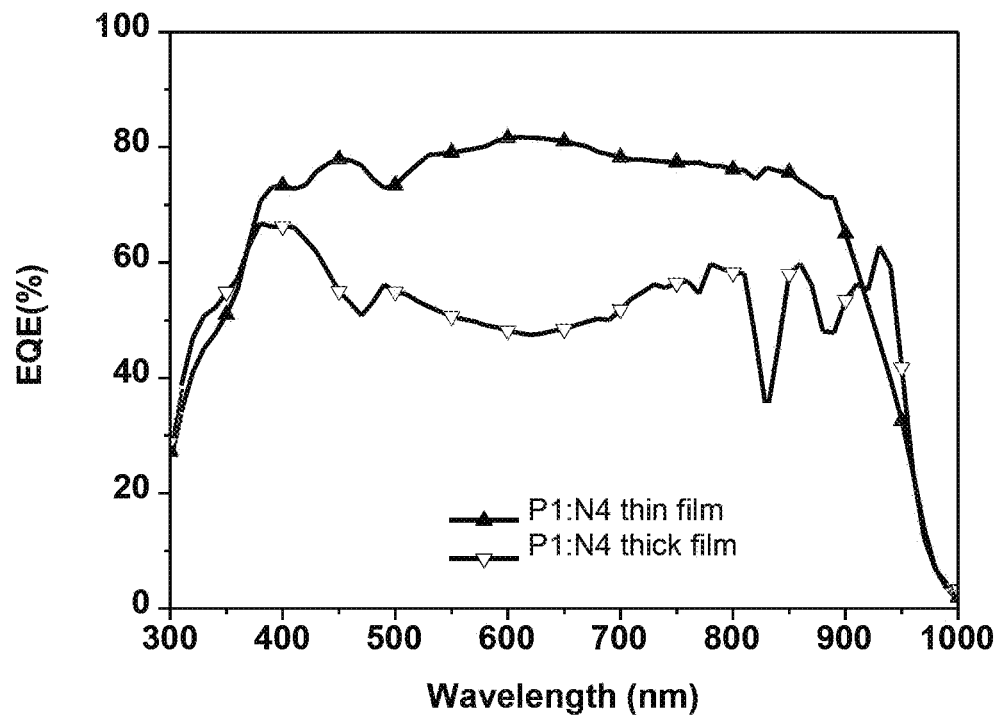
FIG. 13 shows external quantum efficiency of compounds of an embodiment measured at different wavelengths according to the present invention.
Figure 14:
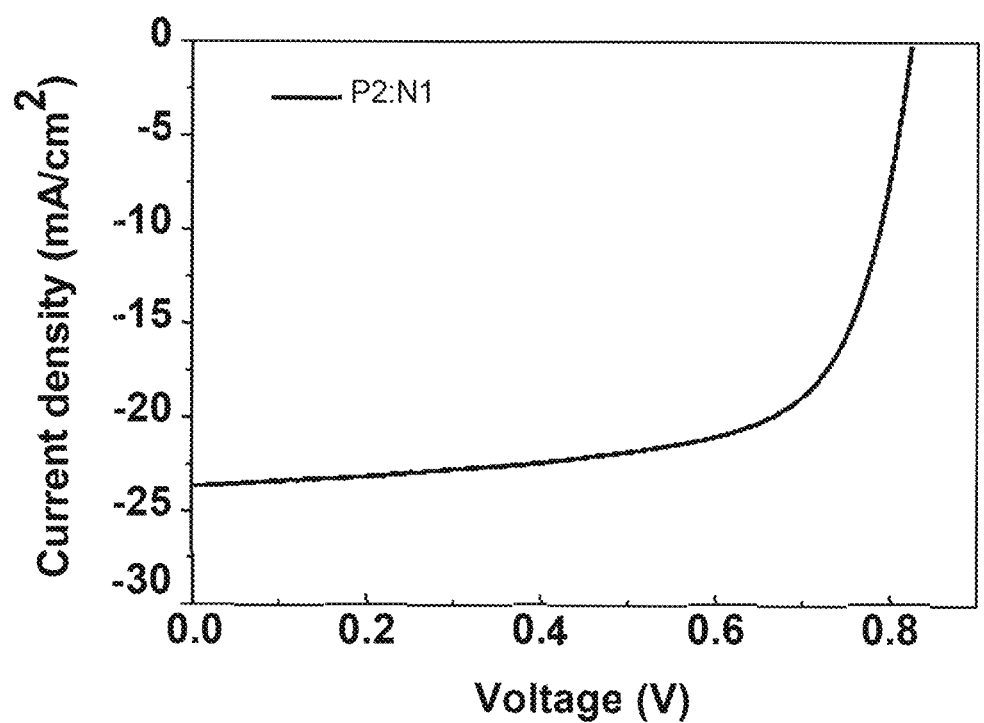
FIG. 14 shows a current density versus voltage curve of an organic photovoltaic (OPV) cell having a compound of an embodiment according to the present invention.

The measurement results are shown in List 1 with reference to FIG. 10 and FIG. 11.

List 1: results of the measurement
Properties of compound N1 and compound N2

| Materials | $\lambda_{soln}^{max}$ (nm) | $\lambda_{film}^{max}$ (nm) | $\lambda_{film}^{onset}$ (nm) | ε (10$^5$ cm$^{-1}$ M$^{-1}$) | $E_g^{opt}$ (eV) | HOMO (eV) | LUMO (eV) |
|---|---|---|---|---|---|---|---|
| N1 | 743 | 840 | 941 | 1.38 | 1.32 | −5.68 | −4.36 |
| N2 | 756 | 852 | 945 | 1.49 | 1.31 | −5.73 | −4.42 |

Embodiment 7: OPD Performance Test

Use a piece of glass that has sheet resistance and a patterned ITO (indium tin oxide) coating as a substrate. The substrate is processed by sonication in a neutral detergent, de-ionized water, acetone, and isopropyl alcohol in turn. Each step in the solution takes 15 minutes. The washed substrate is further processed by an UV—$O_3$ cleaner for 15 minutes. A topcoat made of aluminum-doped zinc oxide nanoparticle (AZO) is formed on the ITO substrate by spin coating at 2000 rpm for 40 seconds and then baked at 120° C. for 5 minutes in the atmosphere. Prepare a solution for the active layer in o-xylene (weight ratio of donor polymer to acceptor small molecules is 1:1.2~1:1.5) and the concentration of the polymer is 12~16 mg/ml. In order to dissolve the polymer completely, the solution for the active layer is heated and stirred on the heating plate at 100° C. for at least 3 hours. Then the solution for the active layer is filtered by polytetrafluoroethylene (PTFE) filter membrane (pore size 0.45-1.2 μm) and heated for 1 hour. Later the solution is placed at room temperature to cool down for the subsequent coating. The thickness of the film is controlled within 500~1000 nm by the spin coating speed. Then the composite film is treated by annealing at 100° C. for 5 minutes and sent to an evaporator. Under vacuum evaporation at 3×10−6 Torr, a molybdenum trioxide ($MoO_3$) thin film with a thickness of 8 nm is deposited and used as an anode intermediate layer. Use Keithley™ 2400 source meter to detect a reverse current ($I_D$) in the dark (total absence of light), when a reverse bias voltage (−8V) is applied. Then use a solar simulator (with an AM1.5G filter and a xenon lamp, 100 mW cm$^{-2}$) to measure photocurrent ($I_{ph}$ in the air at room temperature. The light intensity is calibrated by a standard silicon diode with a KG5 filter used as a reference cell for spectral mismatch correction. External quantum efficiency (EQE) is measured by an external quantum efficiency measurement system with a wavelength range of 300-1100 nm (bias voltage 0~−8V). A calibration measurement is obtained using a calibrated silicon photodetector (300~1100 nm) and a germanium photodetector (1100~1800 nm). The measurement results are shown in list 2.

List 2: performance test results of OPD

| BHJ | Thickness (nm) | $I_D$@-0.1 V (A cm$^{-2}$) | $I_D$@-8 V (A cm$^{-2}$) | $I_{ph}$@-8 V (mA cm$^{-2}$) | EQE 850 nm | EQE 940 nm |
|---|---|---|---|---|---|---|
| PFT-OEHp:Y6[1] | ~200 | 1.0 × 10$^{-7}$ | — | — | ~65% (@-0.1 V) | ~5% (@-0.1 V) |
| P1:N2 | ~500 | 4.9 × 10$^{-9}$ | 2.7 × 10$^{-7}$ | 29.4 | 76% (@-8 V) | 40% (@-8 V) |
|  | ~1000 | 1.9 × 10$^{-8}$ | 4.9 × 10$^{-8}$ | 33.3 | 58% (@-8 V) | 59% (@-8 V) |

The structural formula of compound P1 mixed with compound N2 in the list 2

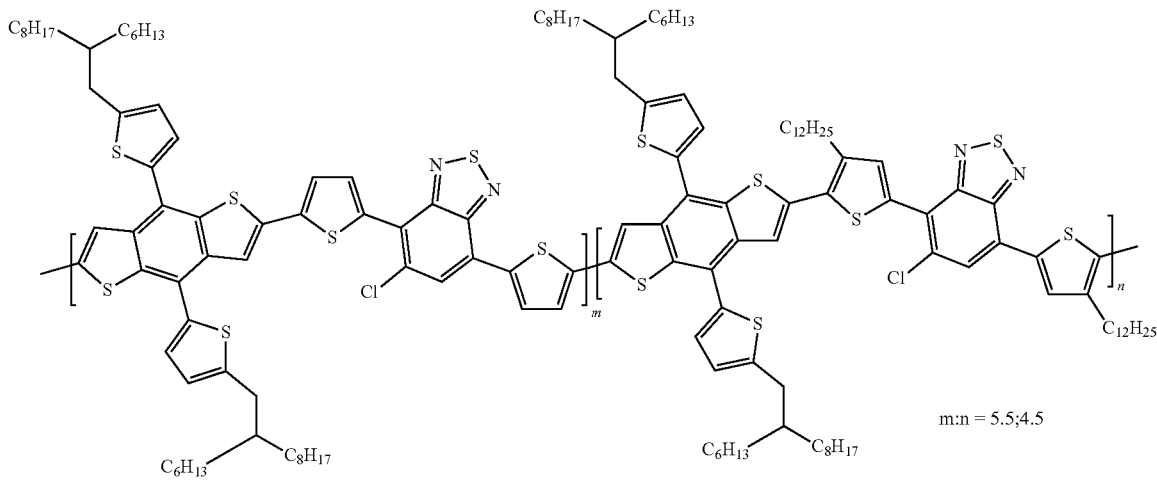

P1 m:n = 5.5;4.5

The structure of compound P1 is the same as polymer 10A revealed in the U.S. Pat. No. 8,772,442 B2.

Embodiment 8: OPV Performance Test

Use a piece of glass provided with both sheet resistance and a patterned ITO (indium tin oxide) coating as a substrate. The substrate is processed by ultrasonic vibration treatment in a neutral detergent, de-ionized water, acetone, and isopropyl alcohol in turn. Each step in respective solutions takes 15 minutes. The washed substrate is further processed by an UV—$O_3$ cleaner for 15 minutes. A topcoat made of zinc oxide (diethylzinc solution, 15 wt. % in toluene, diluted with tetrahydrofuran) is formed on the ITO substrate by spin coating at 5000 rpm for 30 seconds and then baked at 120° C. for 20 minutes in the air. Prepare a solution for the active layer in o-xylene (weight ratio of donor polymer to acceptor small molecules is 1:1.2~1:1.5) and the concentration of the polymer is 8~10 mg/ml. In order to dissolve the polymer completely, the solution for the active layer is heated and stirred on the heating plate at 100° C. for at least 3 hours. Then the solution for the active layer is placed at room temperature to cool down for the subsequent coating. The thickness of the film is controlled to about 100 nm by the spin coating speed. Next, the composite film is treated by annealing at 120° C. for 5 minutes and sent to an evaporator. Under vacuum evaporation at $3\times10^{-6}$ Torr, a molybdenum trioxide ($MoO_3$) thin film (8 nm) is deposited and used as an anode intermediate layer. A solar simulator (with an AM1.5G filter and a xenon lamp, 100 mW $cm^2$) is used to measure J-V (current density versus voltage) characteristics of the organic photovoltaic device in the air at room temperature. The light intensity is calibrated by a standard silicon diode with a KG5 filter used as a reference cell for spectral mismatch correction. A Keithley 2400 source meter unit was used to record J-V characteristics. A typical cell has an active area of 4 $mm^2$ while the active area is defined as the area where a metal shield with pores is aligned with the device. The power conversion efficiency (PCE) is an average value of the measurement results obtained at 4 effective points on the device. The measurement results are shown in the list 3.

List 3: performance test results of OPV

| BHJ | $V_{oc}$ (eV) | $J_{sc}$ (mA/$cm^2$) | FF (%) | PCE (%) |
|---|---|---|---|---|
| P2:N1 | 0.83 | 23.7 | 68.1 | 13.4 |

The structural formula of compound P2 mixed with compound N1 in the list 3.

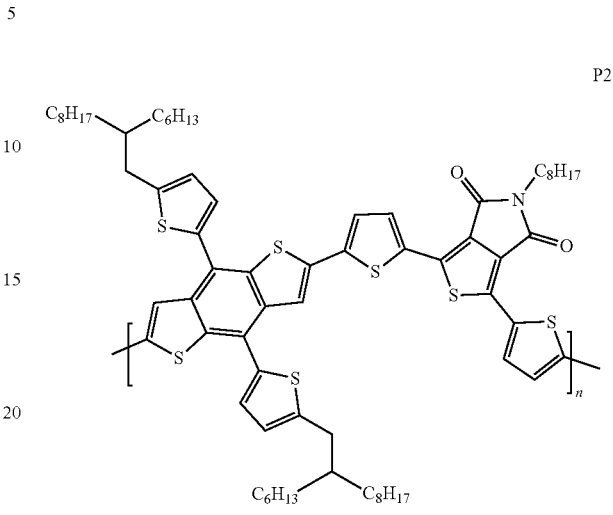

The structure of compound P2 is shown in *Joule* 2020, 4, 189-206.

From the above test results, the HOMO value of the present non-fullerene acceptor compounds containing benzoselenadiazole is increased compared with non-fullerene acceptors available now. While being applied to OPD, the present non-fullerene acceptor compounds containing benzoselenadiazole not only has a quite low leakage current but also has high external quantum efficiency at 940 nm. While being applied to OPV, the present non-fullerene acceptor compounds containing benzoselenadiazole provides good power conversion efficiency.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalent.

What is claimed is:

1. A non-fullerene acceptor compound containing benzoselenadiazole having the following formula:

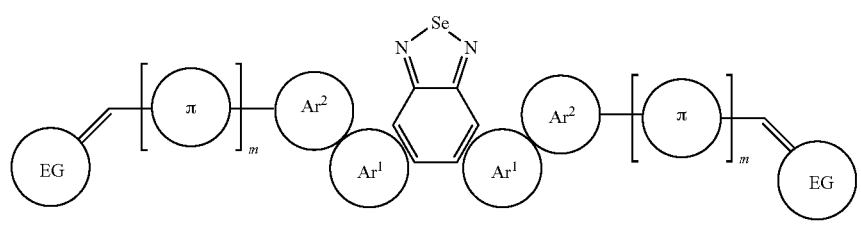

wherein Ar¹ is a five-membered heterocyclic ring;
Ar² is a monocyclic or polycyclic, C5, C6, C8, C9, or C10 heteroaromatic derivative;
π is a monocyclic or polycyclic, C5, C6, C7, C8 or C9 heteroaromatic derivative, wherein
m=0-5; and
EG is a monocyclic or polycyclic derivative containing a ketone group and electron-withdrawing group.

2. The non-fullerene acceptor compound containing benzoselenadiazole according to claim 1, wherein Ar¹ is selected from the group consisting of

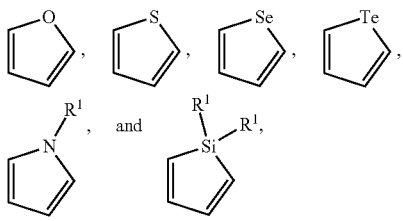

which the substituent R¹ of Ar¹ is selected from the group consisting of C1-C30 linear alkyl, C1-C30 branched alkyl, C1-C30 silyl, C1-C30 ester, C1-C30 alkoxy, C1-C30 alkylthio, C1-C30 haloalkyl, C1-C30 alkyl substituted with alkene groups or alkyne groups, C1-C30 cyanoalkyl, C1-C30 nitroalkyl, C1-C30 hydroxyalkyl, C1-C30 keto-alkyl, and halogen.

3. The non-fullerene acceptor compound containing benzoselenadiazole according to claim 1, wherein Ar² is selected from the group consisting of

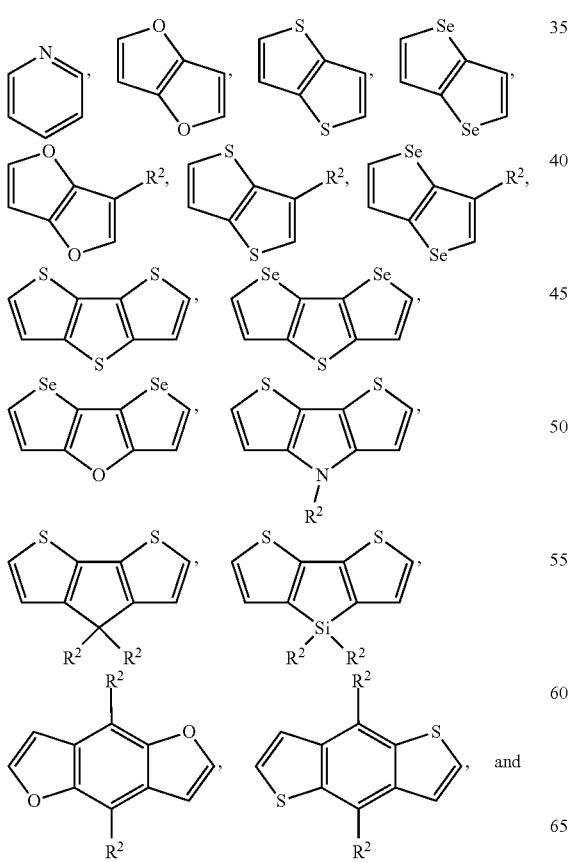

-continued

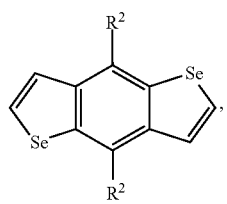

which the substituent R² of Ar² is selected from the group consisting of C1-C30 linear alkyl, C1-C30 branched alkyl, C1-C30 silyl, C1-C30 ester, C1-C30 alkoxy, C1-C30 alkylthio, C1-C30 haloalkyl, C1-C30 alkyl substituted with alkene groups or alkyne groups, C1-C30 cyanoalkyl, C1-C30 nitroalkyl, C1-C30 hydroxyalkyl, C1-C30 keto-alkyl, halogen, benzene ring containing R¹, five-membered heterocycle containing R¹, and six-membered heterocycle containing R¹, R¹ is selected from the group consisting of C1-C30 linear alkyl, C1-C30 branched alkyl, C1-C30 silyl, C1-C30 ester, C1-C30 alkoxy, C1-C30 alkylthio, C1-C30 haloalkyl, C1-C30 alkyl substituted with alkene groups or alkyne groups, C1-C30 cyanoalkyl, C1-C30 nitroalkyl, C1-C30 hydroxyalkyl, C1-C30 keto-alkyl, and halogen.

4. The non-fullerene acceptor compound containing benzoselenadiazole according to claim 1, wherein the π is selected from the group consisting of

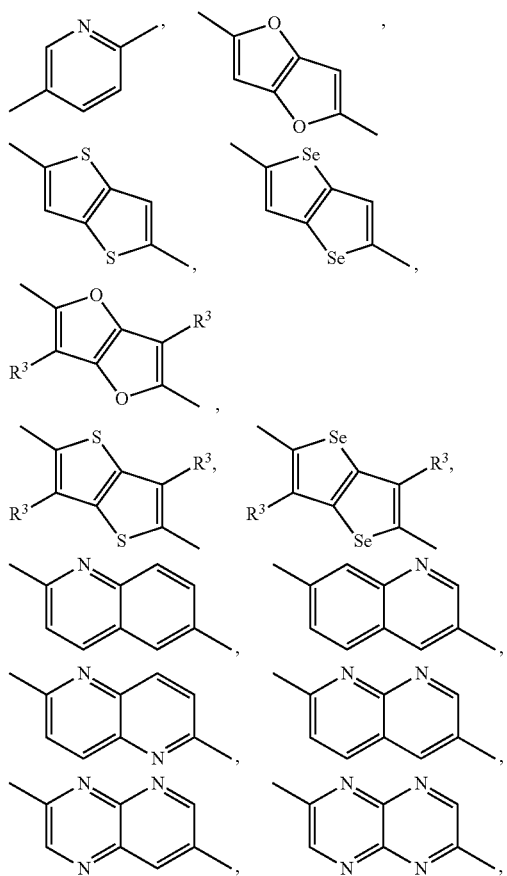

-continued

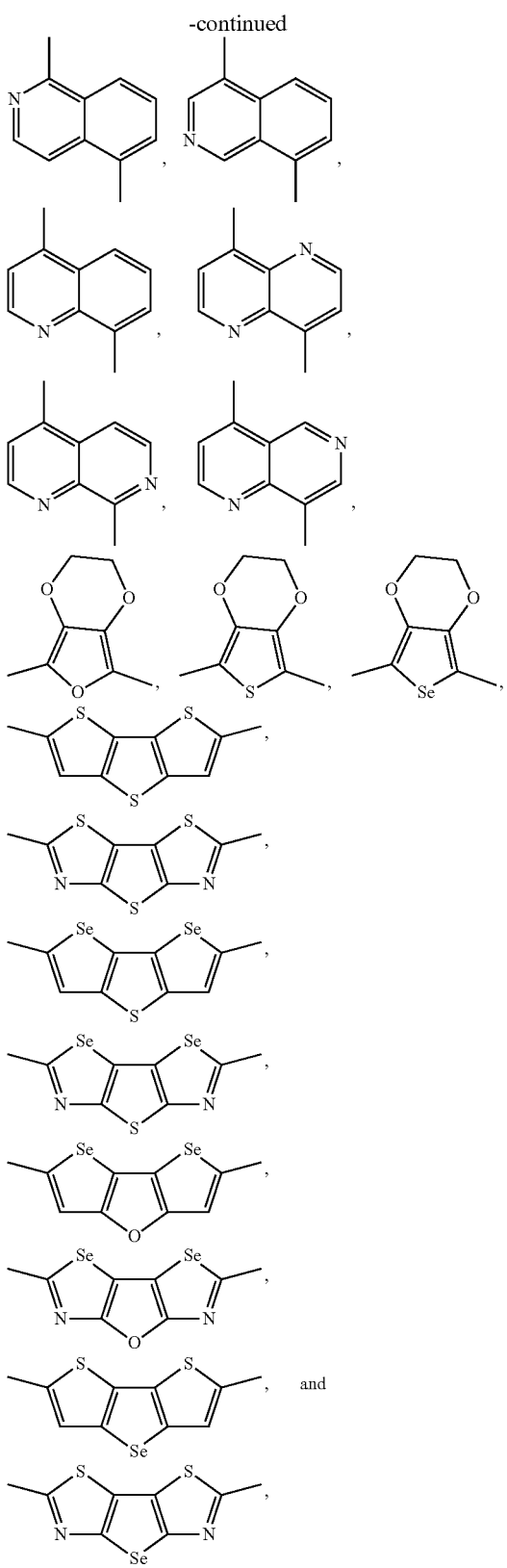

which the substituent R³ of π is selected from the consisting of C1-C30 linear alkyl, C1-C30 branched alkyl, C1-C30 silyl, C1-C30 ester, C1-C30 alkoxy, C1-C30 alkylthio, C1-C30 haloalkyl, C1-C30 alkyl substituted with alkene groups or alkyne groups, C1-C30 cyanoalkyl, C1-C30 nitroalkyl, C1-C30 hydroxyalkyl, C1-C30 keto-alkyl, and halogen.

5. The non-fullerene acceptor compound containing benzoselenadiazole according to claim 1, wherein the EG is selected from the group consisting of

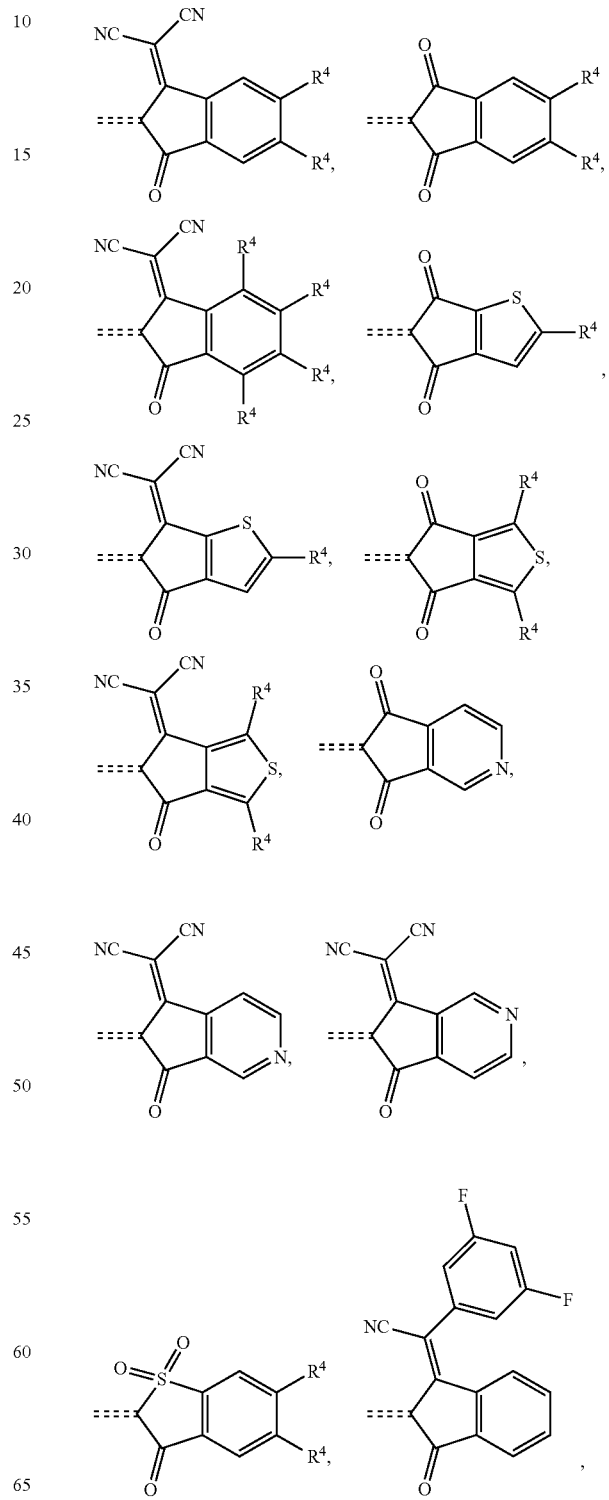

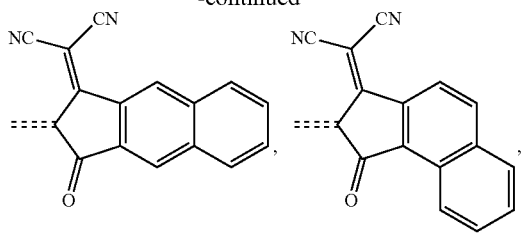

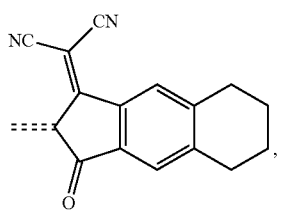

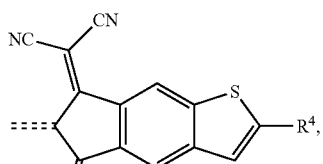

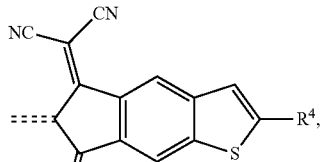

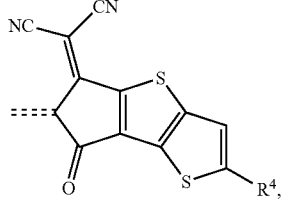

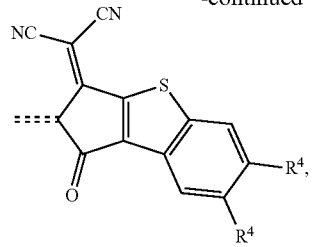

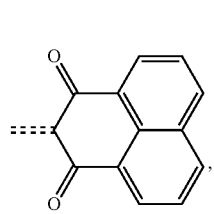, and 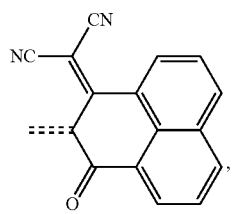, which the substituent $R^4$ of EG is selected from the group consisting of hydrogen atom, halogen, C1-C20 alkyl, C1-C20 alkoxy, C1-C20 carbonyl, C1-C20 ester, and C1-C20 cyano.

6. An organic optoelectronic device comprising:

a substrate;

a bottom electrode disposed on the substrate;

a top electrode arranged opposite to the bottom electrode; and an intermediate layer which is mounted between the bottom electrode and the top electrode and including a first carrier transport layer comprising molybdenum trioxide ($MoO_3$), a second carrier transport layer comprising zinc oxide (ZnO), and an active layer which is arranged between the first carrier transport layer and the second carrier transport layer and including a polymer donor and a non-fullerene acceptor compound containing benzoselenadiazole having the following structural formula

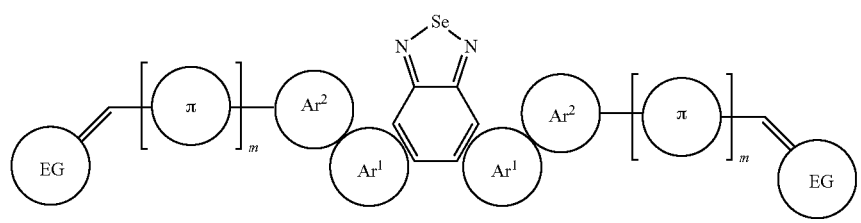

wherein Ar¹ is a five-membered heterocyclic ring;
Ar² is a monocyclic or polycyclic, C5, C6, C8, C9, or C10 heteroaromatic derivative;
π is a monocyclic or polycyclic, C5, C6, C7, C8 or C9 heteroaromatic derivative, wherein
m=0-5; and
EG is a monocyclic or polycyclic derivative containing a ketone group and electron-withdrawing group.

7. The organic optoelectronic device according to claim 6, wherein the active layer is arranged over the first carrier transport layer and the second carrier transport layer is disposed over the active layer.

8. The organic optoelectronic device according to claim 6, wherein the active layer is arranged over the second carrier transport layer and the first carrier transport layer is disposed over the active layer.

9. The organic optoelectronic device according to claim 6, wherein the Ar¹ is selected from the group consisting of

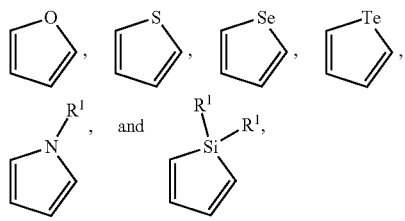

which the substituent R¹ of Ar¹ is selected from the group consisting of C1-C30 linear alkyl, C1-C30 branched alkyl, C1-C30 silyl, C1-C30 ester, C1-C30 alkoxy, C1-C30 alkylthio, C1-C30 haloalkyl, C1-C30 alkyl substituted with alkene groups or alkyne groups, C1-C30 cyanoalkyl, C1-C30 nitroalkyl, C1-C30 hydroxyalkyl, C1-C30 keto-alkyl, and halogen.

10. The organic optoelectronic device according to claim 6, wherein the Ar² is selected from the group consisting of:

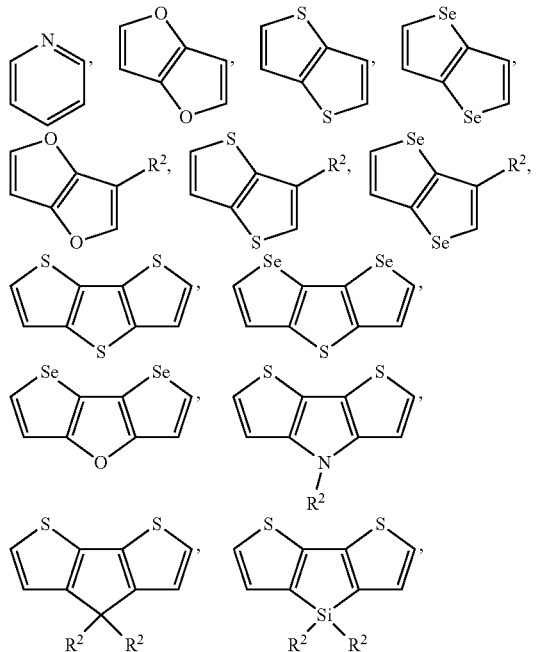

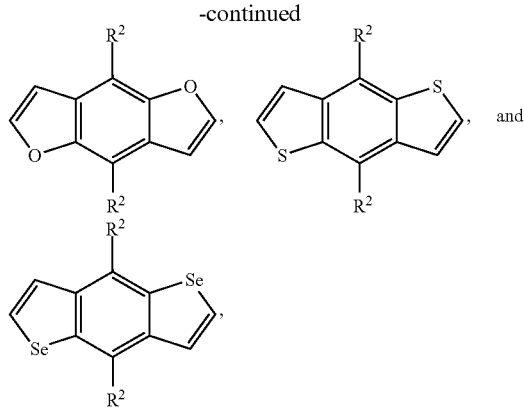

which the substituent R² of Ar² is selected from the group consisting of C1-C30 linear alkyl, C1-C30 branched alkyl, C1-C30 silyl, C1-C30 ester, C1-C30 alkoxy, C1-C30 alkylthio, C1-C30 haloalkyl, C1-C30 alkyl substituted with alkene groups or alkyne groups, C1-C30 cyanoalkyl, C1-C30 nitroalkyl, C1-C30 hydroxyalkyl, C1-C30 keto-alkyl, halogen, benzene ring containing R¹, five-membered heterocycle containing R¹, and six-membered heterocycle containing R¹, R¹ is selected from the group consisting of C1-C30 linear alkyl, C1-C30 branched alkyl, C1-C30 silyl, C1-C30 ester, C1-C30 alkoxy, C1-C30 alkylthio, C1-C30 haloalkyl, C1-C30 alkyl substituted with alkene groups or alkyne groups, C1-C30 cyanoalkyl, C1-C30 nitroalkyl, C1-C30 hydroxyalkyl, C1-C30 keto-alkyl, and halogen.

11. The organic optoelectronic device according to claim 6, wherein the π is selected from the group consisting of

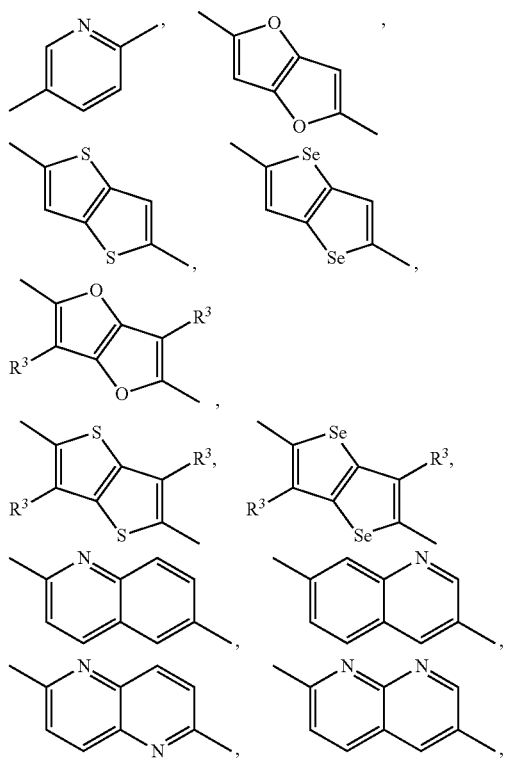

-continued

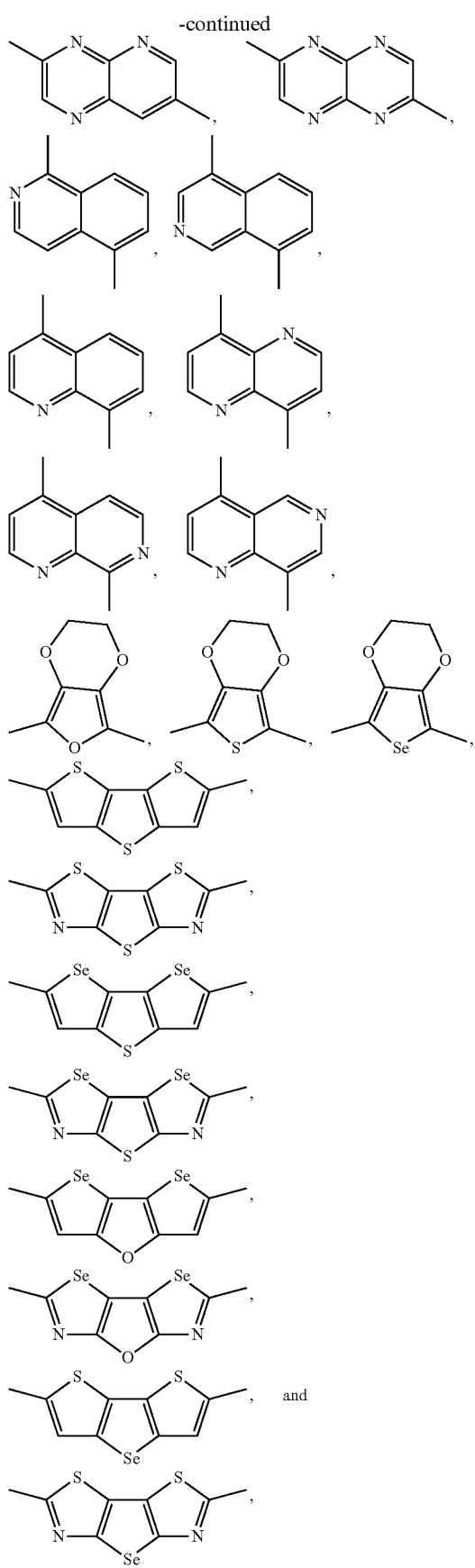

and which the substituent R³ of the π is selected from the consisting of C1-C30 linear alkyl, C1-C30 branched alkyl, C1-C30 silyl, C1-C30 ester, C1-C30 alkoxy, C1-C30 alkylthio, C1-C30 haloalkyl, C1-C30 alkyl substituted with alkene groups or alkyne groups, C1-C30 cyanoalkyl, C1-C30 nitroalkyl, C1-C30 hydroxyalkyl, C1-C30 keto-alkyl, and halogen.

12. The organic optoelectronic device according to claim 6, wherein the EG is selected from the group consisting of

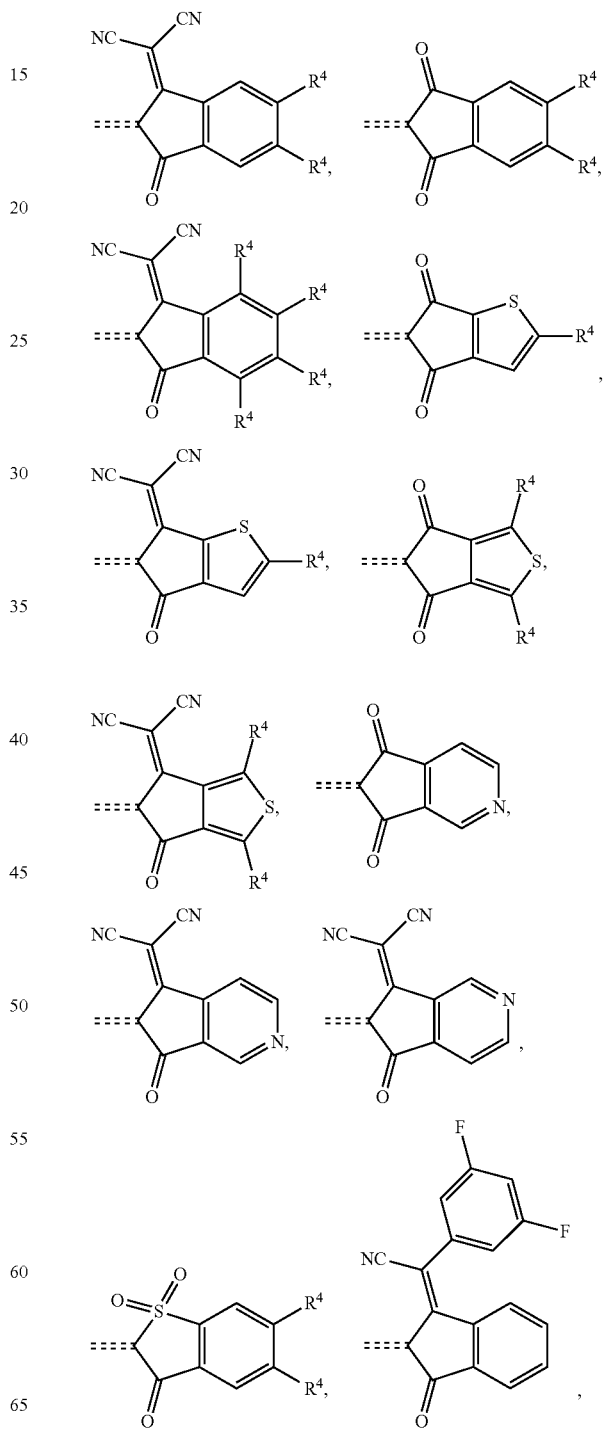

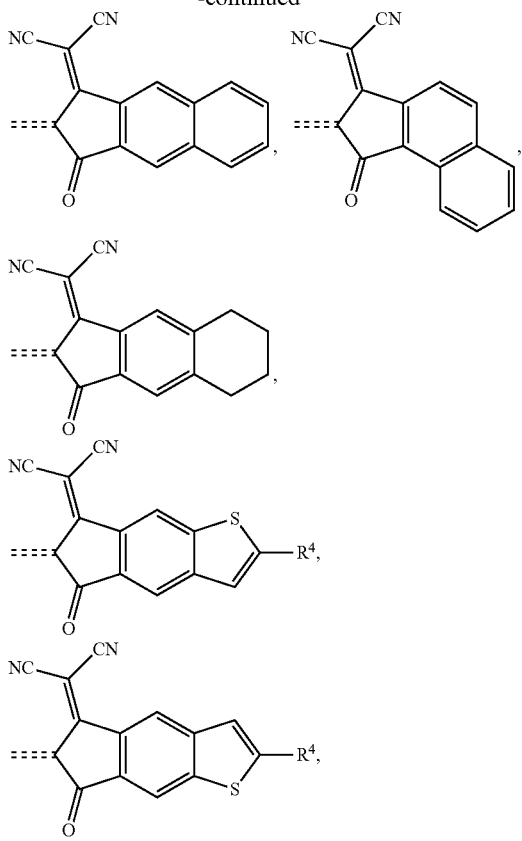
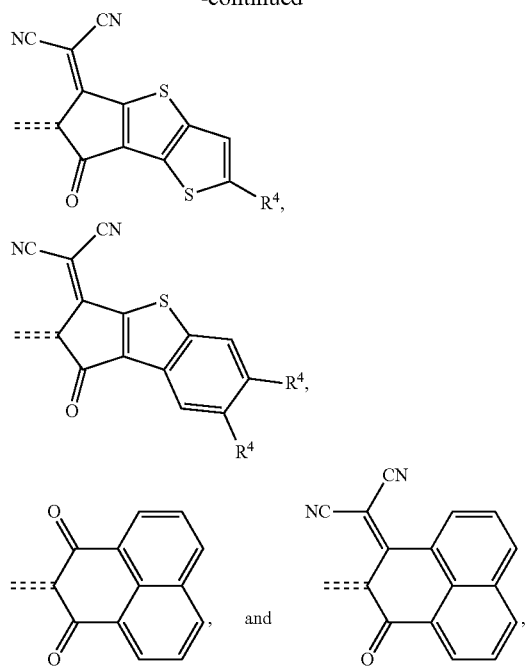
which the substituent $R^4$ of EG is selected from the group consisting of hydrogen atom, halogen, C1-C20 alkyl, C1-C20 alkoxy, C1-C20 carbonylalkyl, C1-C20 ester, and C1-C20 cyano.
* * * * *